(12) United States Patent
Ogino et al.

(10) Patent No.: US 10,548,877 B2
(45) Date of Patent: Feb. 4, 2020

(54) AROMATIC RING COMPOUND

(71) Applicant: TAKEDA PHARMACEUTICAL COMPANY LIMITED, Osaka-shi, Osaka (JP)

(72) Inventors: Masaki Ogino, Kanagawa (JP); Eiji Kimura, Kanagawa (JP); Shinkichi Suzuki, Kanagawa (JP); Kouji Fuji, Kanagawa (JP); Tomohiro Ohashi, Kanagawa (JP); Makoto Fushimi, Kanagawa (JP); Kei Masuda, Kanagawa (JP); Tatsuki Koike, Kanagawa (JP); Takeshi Wakabayashi, Kanagawa (JP); Jinichi Yonemori, Kanagawa (JP); Masami Yamada, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 16/083,295

(22) PCT Filed: Mar. 9, 2017

(86) PCT No.: PCT/JP2017/009529
§ 371 (c)(1),
(2) Date: Sep. 7, 2018

(87) PCT Pub. No.: WO2017/155050
PCT Pub. Date: Sep. 14, 2017

(65) Prior Publication Data
US 2019/0083467 A1 Mar. 21, 2019

(30) Foreign Application Priority Data

Mar. 11, 2016 (JP) .................................. 2016-048866
Jul. 6, 2016 (JP) .................................. 2016-134234

(51) Int. Cl.
*A61K 31/4192* (2006.01)
*A61K 31/415* (2006.01)
(Continued)

(52) U.S. Cl.
CPC ........ *A61K 31/4192* (2013.01); *A61K 31/415* (2013.01); *A61K 31/4155* (2013.01); *A61K 31/427* (2013.01); *A61K 31/4406* (2013.01); *A61K 31/4439* (2013.01); *A61P 25/16* (2018.01); *A61P 25/18* (2018.01); *A61P 25/20* (2018.01); *A61P 25/28* (2018.01); *C07D 213/56* (2013.01); *C07D 231/12* (2013.01); *C07D 249/06* (2013.01); *C07D 401/04* (2013.01); *C07D 405/12* (2013.01); *C07D 405/14* (2013.01); *C07D 413/12* (2013.01); *C07D 417/12* (2013.01)

(58) Field of Classification Search
CPC ............ A61K 31/4192; A61K 31/415; A61K 31/4155; A61K 31/427; A61K 31/4406; A61K 31/4439; A61P 25/20; A61P 25/28; A61P 25/18; A61P 25/16; C07D 213/56; C07D 231/12; C07D 249/06; C07D 401/04; C07D 405/12; C07D 405/14; C07D 413/12; C07D 417/12
See application file for complete search history.

(56) References Cited

U.S. PATENT DOCUMENTS

| | | | |
|---|---|---|---|
| 7,064,124 B2 * | 6/2006 | Suzuki .................... | C07C 65/24 514/239.5 |
| 9,403,802 B2 | 8/2016 | Sakamoto et al. | |

(Continued)

FOREIGN PATENT DOCUMENTS

| | | |
|---|---|---|
| WO | 00/61569 | 10/2000 |
| WO | 2012/114268 | 8/2012 |

(Continued)

OTHER PUBLICATIONS

International Search Report issued in International Application No. PCT/JP2017/009529, dated May 23, 2017, 3 pages.

(Continued)

*Primary Examiner* — Timothy R Rozof
(74) *Attorney, Agent, or Firm* — Hamre, Schumann, Mueller & Larson, P.C.

(57) ABSTRACT

Provided is a compound having a cholinergic muscarine M1 receptor positive allosteric modulator activity. A compound represented by the formula (I):

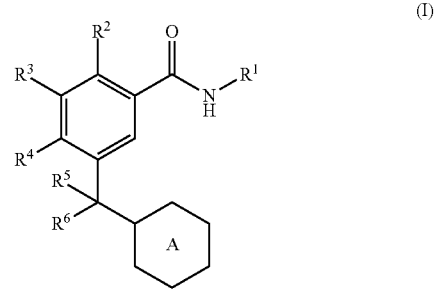

wherein each symbol is as described in the DESCRIPTION, or a salt thereof has a cholinergic muscarine M1 receptor positive allosteric modulator activity, and is useful as a prophylactic or therapeutic drug for Alzheimer's disease, schizophrenia, pain, sleep disorder, Parkinson's disease dementia, dementia with Lewy bodies and the like.

11 Claims, No Drawings

(51) Int. Cl.
  *A61K 31/4155*   (2006.01)
  *A61K 31/427*    (2006.01)
  *A61K 31/4406*   (2006.01)
  *A61K 31/4439*   (2006.01)
  *A61P 25/20*     (2006.01)
  *A61P 25/28*     (2006.01)
  *A61P 25/18*     (2006.01)
  *A61P 25/16*     (2006.01)
  *C07D 213/56*    (2006.01)
  *C07D 231/12*    (2006.01)
  *C07D 249/06*    (2006.01)
  *C07D 401/04*    (2006.01)
  *C07D 405/12*    (2006.01)
  *C07D 405/14*    (2006.01)
  *C07D 413/12*    (2006.01)
  *C07D 417/12*    (2006.01)

(56) References Cited

U.S. PATENT DOCUMENTS

| | | |
|---|---|---|
| 9,777,005 B2 | 10/2017 | Sugimoto et al. |
| 2010/0292203 A1 | 11/2010 | Zhu et al. |
| 2012/0276118 A1 | 11/2012 | Zhu et al. |
| 2015/0126487 A1 | 5/2015 | Sakamoto et al. |
| 2015/0307497 A1 | 10/2015 | Sugimoto et al. |
| 2017/0081332 A1 | 3/2017 | Sugimoto et al. |
| 2017/0121308 A1 | 5/2017 | Ogino et al. |
| 2018/0303841 A1 | 10/2018 | Sugimoto et al. |

FOREIGN PATENT DOCUMENTS

| | | |
|---|---|---|
| WO | 2013/129622 | 9/2013 |
| WO | 2014/077401 | 5/2014 |
| WO | 2015/110370 | 7/2015 |
| WO | 2015/163485 | 10/2015 |
| WO | 2015/174534 | 11/2015 |
| WO | 2015/175171 | 11/2015 |
| WO | 2015/190564 | 12/2015 |
| WO | 2016/009297 | 10/2016 |
| WO | 2016/208775 | 12/2016 |

OTHER PUBLICATIONS

Davoren, et al. "Discovery of the Potent and Selective M1 PAM-Agonist N-[(3R,4S)-3-Hydroxytetrahydro-2H-pyran-4-yl]-5-methyl-4-[4-(1,3-thiazol-4-yl)benzyl]pyridine-2-carboxamide (PF-06767832): Evaluation of Efficacy and Cholinergic Side Effects", Journal of Medicinal Chemistry, vol. 59, 2016, pp. 6313-6328.

Wess, et al., "Mascarinic acetylcholine receptors: mutant mice provide new insights for drug development", Nature Reviews Drug Discovery, vol. 6, Sep. 2007, pp. 721-733.

Kuduk, et al., "Novel M 1 allosteric ligands: a patent review", Expert Opinion on Therapeutic Patents, vol. 22, No. 12, Oct. 23, 2012, pp. 1385-1398.

Extended European Search Report issued in European Application No. 17763390.6, dated Oct. 2, 2019, 10 pages.

* cited by examiner

AROMATIC RING COMPOUND

TECHNICAL FIELD

The present invention relates to a heterocyclic compound which has a cholinergic muscarinic M1 receptor positive allosteric modulator activity and may be useful as a medicament such as an agent for the prophylaxis or treatment of Alzheimer's disease, schizophrenia, pain, sleep disorder, Parkinson's disease dementia, dementia with Lewy bodies and the like. As used herein, the positive allosteric modulator activity refers to an action to potentiate receptor function by binding at a different site from that of an endogenous activator (acetylcholine for this receptor).

BACKGROUND OF THE INVENTION

Acetylcholine is a neurotransmitter that induces signal transduction in the central nervous system and the neuromuscular connections (the parasympathetic nerve and motor nerve). In the central nervous system, nuclei of origin of the acetylcholine neuron are in the brain stem and forebrain, and those acetylcholine neurons project to cerebral cortex, hippocampus, and limbic area. In addition, some interneurons in some brain areas such as striatum utilize acetylcholine as a neurotransmitter. Acetylcholine receptor is classified into a ligand dependent-ion channel (cholinergic nicotinic receptor) and a G-protein-coupled receptor (cholinergic muscarinic receptor). The cholinergic muscarinic receptor is one kind of receptor for excitatory neurotransmitter, acetylcholine, and was named based on the selective activation of the receptor by muscarine. The muscarinic receptor is further classified into subtypes of M1 to M5. The M1 receptor is known to be mainly distributed in the brain, and deeply involved particularly in learning, memory, sleep, neuropathic pain, and the like. The importance of cholinergic muscarinic M1 receptor in brain physiology is well known, and a compound which enhances M1 receptor function is expected to be useful as an agent for the prophylaxis or treatment of mental diseases, neurodegenerative diseases, memory disorders, pain, sleep disorders, Parkinson's disease dementia, dementia with Lewy bodies and the like (non-patent document 1).

Patent document 1 discloses the following compound as a compound having an autotaxin (ATX) inhibitory activity and useful for the treatment of cancer, chronic inflammatory disease, neuropathic pain, fibrosis, thrombus and the like.

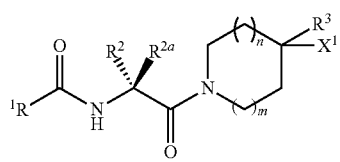

wherein each symbol is as defined in the document.

Patent document 2 discloses the following compound as a compound having a P2X7 receptor antagonist activity and useful for the treatment of pain, neurodegenerative and neuroinflammatory diseases (e.g., Alzheimer's disease and other dementia such as dementia with Lewy bodies, Huntington's disease, Parkinson's disease and the like), bone and articular diseases and the like.

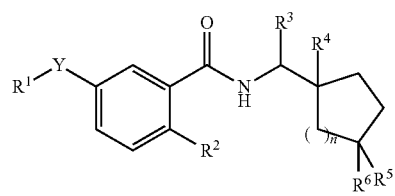

wherein each symbol is as defined in the document.

Patent document 3 discloses the following compound as a compound having a P2X7 receptor antagonist activity and useful for the treatment of rheumatoid arthritis, arthritis deformans, psoriasis, Alzheimer's disease and the like.

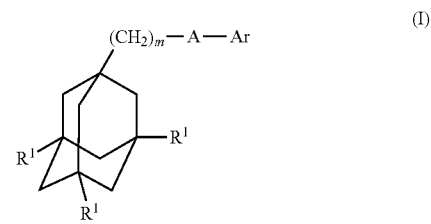

wherein each symbol is as defined in the document.

Patent document 4 discloses the following compound as a compound having a cholinergic muscarine M1 receptor positive allosteric modulator (M1PAM) activity and useful for the treatment of Alzheimer's disease, schizophrenia or psychosis, pain, addiction, sleep disorder, cognitive dysfunction, Parkinson's disease, dyskinesia and the like.

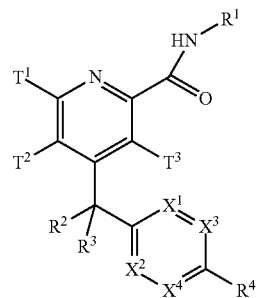

wherein each symbol is as defined in the document.

Patent document 5 discloses the following compound as a compound having an M1PAM activity and useful for the treatment of Alzheimer's disease, schizophrenia, pain, sleep disorder and the like.

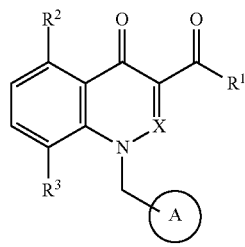

wherein each symbol is as defined in the document.

Patent document 6 discloses the following compound as a compound having an M1PAM activity and useful for the treatment of Alzheimer's disease, schizophrenia, pain, sleep disorder and the like.

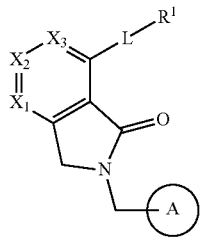

wherein each symbol is as defined in the document.

Patent document 7 discloses the following compound as a compound having an M1PAM activity and useful for the treatment of Alzheimer's disease, schizophrenia, pain, sleep disorder, Parkinson's disease dementia, dementia with Lewy bodies and the like.

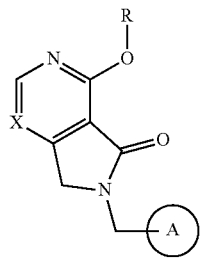

wherein each symbol is as defined in the document.

Patent document 8 discloses the following compound as a compound having an M1PAM activity and useful for the treatment of Alzheimer's disease, schizophrenia, pain, sleep disorder, Parkinson's disease dementia, dementia with Lewy bodies and the like.

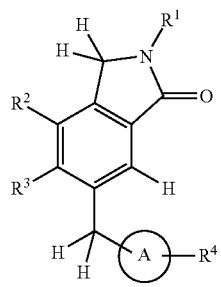

wherein each symbol is as defined in the document.

Patent document 9 discloses the following compound as a compound having an M1PAM activity and useful for the treatment of Alzheimer's disease, schizophrenia, pain, sleep disorder, Parkinson's disease dementia, dementia with Lewy bodies and the like.

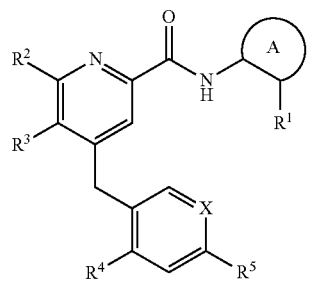

wherein each symbol is as defined in the document.

Furthermore, the following compound A (CAS Registry Number 1240103-23-4) is known.

compound A

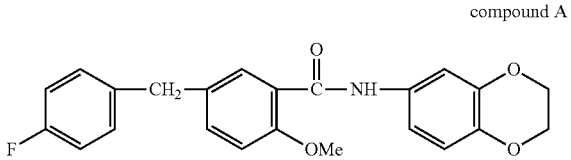 [SMILES: COc1ccc(Cc2ccc(F)cc2)cc1C(=O)Nc1ccc2c(c1)OCCO2]

DOCUMENT LIST

Patent Documents patent document 1: WO 2015/175171
patent document 2: WO 2012/114268
patent document 3: WO 2000/061569
patent document 4: WO 2016/009297
patent document 5: WO 2013/129622
patent document 6: WO 2014/077401
patent document 7: WO 2015/174534
patent document 8: WO 2015/163485
patent document 9: WO 2015/190564

Non-Patent Document non-patent document 1: Nature Reviews Drug Discovery, 2007, 6, 721-733.

SUMMARY OF THE INVENTION

Problems to be Solved by the Invention

The development of a compound having a cholinergic muscarinic M1 receptor (M1 receptor) positive allosteric modulator activity and useful as an agent for the prophylaxis or treatment of for Alzheimer's disease, schizophrenia, pain, sleep disorder, Parkinson's disease dementia, dementia with Lewy bodies and the like is desired.

Means of Solving the Problems

The present inventors have conducted intensive studies in an attempt to solve the aforementioned problems and found that a compound represented by the following formula (I) may have a cholinergic muscarinic M1 receptor positive allosteric modulator activity, which resulted in the completion of the present invention.

Therefore, the present invention relates to the following.
[1] A compound represented by the formula:

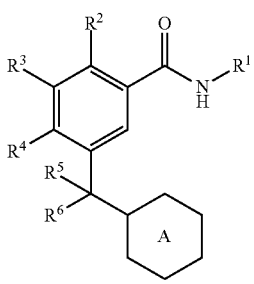

(I)

wherein

R¹ is (A) a C₁₋₆ alkyl group substituted by 1 to 3 substituents selected from (1) a halogen atom, (2) a hydroxy group, (3) an optionally substituted $C_{3-10}$ cycloalkyl group, and (4) an optionally substituted non-aromatic heterocyclic group, (B) an optionally substituted $C_{3-10}$ cycloalkyl group, (C) an optionally substituted $C_{3-10}$ cycloalkenyl group, or (D) an optionally substituted non-aromatic heterocyclic group;

R² is a fluorine atom or an optionally substituted $C_{1-6}$ alkoxy group;

R³ is a hydrogen atom, a halogen atom, a cyano group, an optionally substituted $C_{L-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted $C_{3-10}$ cycloalkyl group, or an optionally substituted $C_{3-10}$ cycloalkyloxy group;

R⁴ is a hydrogen atom, a halogen atom, a cyano group, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted $C_{3-10}$ cycloalkyl group, or an optionally substituted $C_{3-10}$ cycloalkyloxy group;

R⁵ and R⁶ are each independently a hydrogen atom or a halogen atom; and ring A is an optionally further substituted benzene ring or an optionally further substituted 6-membered aromatic heterocycle (excluding N-(2,3-dihydro-1,4-benzodioxin-6-yl)-5-(4-fluorobenzyl)-2-methoxybenzamide) or a salt thereof (sometimes to be abbreviated as "compound (I)" in the present specification).

[2] The compound of [1], wherein R¹ is an optionally substituted 3- to 8-membered monocyclic non-aromatic heterocyclic group, or a salt thereof.

[3] The compound of [1], wherein R¹ is (A) a $C_{1-6}$ alkyl group substituted by 1 to 3 substituents selected from non-aromatic heterocyclic groups, (B) a non-crosslinked $C_{3-10}$ cycloalkyl group optionally substituted by a hydroxy group, or (C) a 3- to 8-membered monocyclic non-aromatic heterocyclic group optionally substituted by a hydroxy group;

R² is a fluorine atom, or a $C_{1-6}$ alkoxy group optionally substituted by 1 to 3 substituents selected from a halogen atom and a $C_{3-10}$ cycloalkyl group;

R³ is a hydrogen atom, a halogen atom or a $C_{1-6}$ alkyl group;

R⁴ is a cyano group or a $C_{1-6}$ alkyl group;

R⁵ and R⁶ are both hydrogen atoms; and ring A is a benzene ring optionally further substituted by 1 to 3 substituents selected from 5- to 14-membered aromatic heterocyclic groups optionally substituted by 1 to 3 $C_{1-6}$ alkyl groups, or a 6-membered aromatic heterocycle optionally further substituted by 1 to 3 substituents selected from a $C_{1-6}$ alkyl group and a 5- to 14-membered aromatic heterocyclic group optionally substituted by 1 to 3 $C_{1-6}$ alkyl groups, or a salt thereof.

[4] The compound of [1], wherein R¹ is a non-crosslinked $C_{3-10}$ cycloalkyl group optionally substituted by a hydroxy group or a 3- to 8-membered monocyclic non-aromatic heterocyclic group optionally substituted by a hydroxy group;

R² is a fluorine atom or a $C_{1-6}$ alkoxy group;

R³ is a halogen atom or a $C_{1-6}$ alkyl group;

R⁴ is a $C_{1-6}$ alkyl group;

R⁵ and R⁶ are both hydrogen atoms; and ring A is a benzene ring optionally further substituted by 1 to 3 substituents selected from 5- to 14-membered aromatic heterocyclic groups optionally substituted by 1 to 3 $C_{1-6}$ alkyl groups, or a salt thereof.

[5] The compound of [4], wherein R¹ is

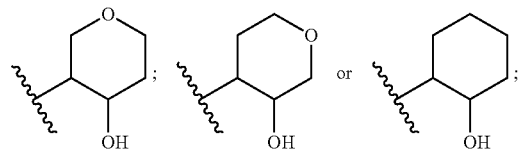

and ring A is a benzene ring optionally further substituted by 1 to 3 substituents selected from 5- or 6-membered monocyclic aromatic heterocyclic groups optionally substituted by 1 to 3 $C_{1-6}$ alkyl groups, or a salt thereof.

[6] The compound of [1], wherein R¹ is

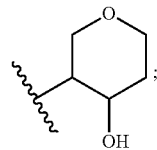 [SMILES: *C1COCCC1O]

R² is a fluorine atom or a $C_{1-6}$ alkoxy group;

R³ is a $C_{1-6}$ alkyl group;

R⁴ is a $C_{1-6}$ alkyl group;

R⁵ and R⁶ are both hydrogen atoms; and ring A is a benzene ring further substituted by a 5- or 6-membered monocyclic aromatic heterocyclic group optionally substituted by one $C_{1-6}$ alkyl group, or a salt thereof.

[7] 2-Fluoro-N-((3S,4S)-4-hydroxytetrahydro-2H-pyran-3-yl)-3,4-dimethyl-5-(4-(1H-pyrazol-1-yl)benzyl)benzamide, or a salt thereof.

[8] N-((3S,4S)-4-hydroxytetrahydro-2H-pyran-3-yl)-2-methoxy-3,4-dimethyl-5-(4-(1-methyl-1H-1,2,3-triazol-4-yl)benzyl)benzamide, or a salt thereof.

[9] A medicament comprising the compound of [1] or a salt thereof.

[10] The medicament of [9], wherein the medicament is a cholinergic muscarinic M1 receptor positive allosteric modulator.

[11] The medicament of [9], wherein the medicament is a prophylactic or therapeutic agent for Alzheimer's disease, schizophrenia, pain, sleep disorder, Parkinson's disease dementia, or dementia with Lewy bodies.

[12] The compound of [1] or a salt thereof for use in the prophylaxis or treatment of Alzheimer's disease, schizophrenia, pain, sleep disorder, Parkinson's disease dementia, or dementia with Lewy bodies.

[13] A method of cholinergic muscarinic M1 receptor positive allosteric modulation in a mammal, comprising administering an effective amount of the compound of [1] or a salt thereof to the mammal.

[14] A method for the prophylaxis or treatment of Alzheimer's disease, schizophrenia, pain, sleep disorder, Parkinson's disease dementia, or dementia with Lewy bodies in a mammal, comprising administering an effective amount of the compound of [1] or a salt thereof to the mammal.

[15] Use of the compound of [1] or a salt thereof in the production of a prophylactic or therapeutic agent for Alzheimer's disease, schizophrenia, pain, sleep disorder, Parkinson's disease dementia, or dementia with Lewy bodies.

Effect of the Invention

The compound of the present invention has a cholinergic muscarinic M1 receptor positive allosteric modulator activity, and is useful as a prophylactic or therapeutic agent for, for example, Alzheimer's disease, schizophrenia, pain, sleep disorder, Parkinson's disease dementia, dementia with Lewy bodies and the like.

DETAILED DESCRIPTION OF THE INVENTION

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "non-cross-linked $C_{3-10}$ cycloalkyl group" include those among the above-mentioned "$C_{3-10}$ cycloalkyl group" and not crosslinked.

In the present specification, examples of the "non-cross-linked $C_{3-10}$ cycloalkyl group" include cyclopropyl, cyclobutyl, cyclopentyl, cyclohexyl, cycloheptyl and cyclooctyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following substituent group A.

[substituent group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl)amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 hetero atoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 hetero atoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 hetero atoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the aforementioned substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbonsulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkylphosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted amino group include an amino group, a mono- or di-(optionally halogenated $C_{1-6}$ alkyl)amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl)amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl)amino group (e.g., N-acetyl-N-methylamino) and a ($C_{1-6}$ alkyl) ($C_{6-14}$ aryl-carbonyl)amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocycly-loxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from substituent group A".

Preferable examples of the optionally substituted silyl group include a tri-$C_{1-6}$ alkylsilyl group (e.g., trimethylsilyl, tert-butyl(dimethyl)silyl).

In the present specification, examples of the "hydrocarbon ring" include a $C_{6-14}$ aromatic hydrocarbon ring, $C_{3-10}$ cycloalkane and $C_{3-10}$ cycloalkene.

In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocycle" include an aromatic heterocycle and a non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi or tricyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiin, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxathiine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepane, diazepane, azepine, azocane, diazocane, oxepane and the like; and 9- to 14-membered fused polycyclic (preferably bi or tricyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "6-membered aromatic heterocycle" include those among the above-mentioned "aromatic heterocycle" and are 6-membered.

Each symbol in the formula (I) is explained below.

$R^1$ is (A) a $C_{1-6}$ alkyl group substituted by 1 to 3 substituents selected from (1) a halogen atom, (2) a hydroxy group, (3) an optionally substituted $C_{3-10}$ cycloalkyl group (preferably, non-crosslinked $C_{3-10}$ cycloalkyl group), and (4) an optionally substituted non-aromatic heterocyclic group, (B) an optionally substituted $C_{3-10}$ cycloalkyl group, (C) an optionally substituted $C_{3-10}$ cycloalkenyl group, or (D) an optionally substituted non-aromatic heterocyclic group (preferably, a 3- to 8-membered monocyclic non-aromatic heterocyclic group).

As the substituent of the "optionally substituted $C_{3-10}$ cycloalkyl group" for $R^1$, a hydroxy group and the like can be mentioned.

As the substituent of the "optionally substituted $C_{3-10}$ cycloalkenyl group" for $R^1$, a hydroxy group and the like can be mentioned.

As the substituent of the "optionally substituted non-aromatic heterocyclic group" for $R^1$, a hydroxy group and the like can be mentioned.

$R^1$ is preferably a $C_{1-6}$ alkyl group (e.g., methyl) substituted by 1 to 3 substituents selected from an optionally substituted non-aromatic heterocyclic group (e.g., tetrahydrofuranyl), an optionally substituted $C_{3-10}$ cycloalkyl group (e.g., cyclopentyl, cyclohexyl), or an optionally substituted non-aromatic heterocyclic group (e.g., tetrahydrofuranyl, tetrahydropyranyl). $R^1$ is more preferably a $C_{1-6}$ alkyl group (e.g., methyl) substituted by 1 to 3 substituents selected from an optionally substituted non-aromatic heterocyclic group (e.g., tetrahydrofuranyl), an optionally substituted non-crosslinked $C_{3-10}$ cycloalkyl group (e.g., cyclopentyl, cyclohexyl), or an optionally substituted 3- to 8-membered monocyclic non-aromatic heterocyclic group (e.g., tetrahydrofuranyl, tetrahydropyranyl). $R^1$ is further preferably (A) a $C_{1-6}$ alkyl group (e.g., methyl) substituted by 1 to 3 substituents selected from a non-aromatic heterocyclic group (e.g., tetrahydrofuranyl), (B) a non-crosslinked $C_{3-10}$ cycloalkyl group (e.g., cyclopentyl, cyclohexyl) optionally substituted by a hydroxy group, or (C) a 3- to 8-membered monocyclic non-aromatic heterocyclic group (e.g., tetrahydrofuranyl, tetrahydropyranyl) optionally substituted by a hydroxy group. $R^1$ is further more preferably a non-crosslinked $C_{3-10}$ cycloalkyl group (e.g., cyclohexyl) optionally substituted by a hydroxy group, or a 3- to 8-membered monocyclic non-aromatic heterocyclic group (e.g., tetrahydropyranyl) optionally substituted by a hydroxy group. $R^1$ is particularly preferably a 3- to 8-membered monocyclic non-aromatic heterocyclic group (e.g., tetrahydropyranyl) optionally substituted by a hydroxy group.

In another embodiment of the present invention, $R^1$ is preferably

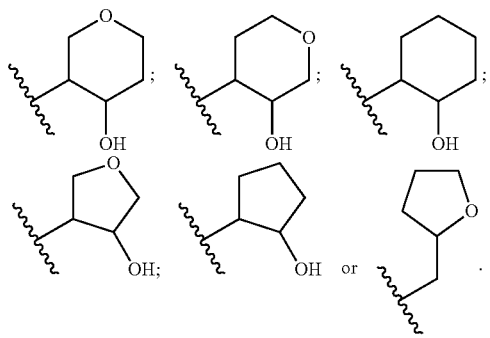

$R^1$ is more preferably

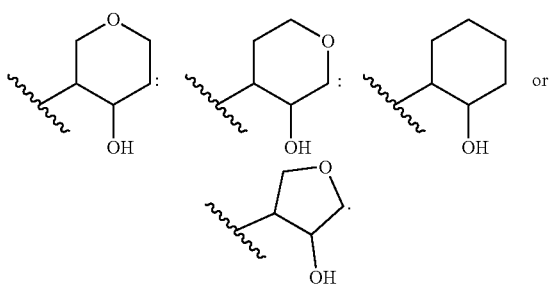

$R^1$ is further preferably

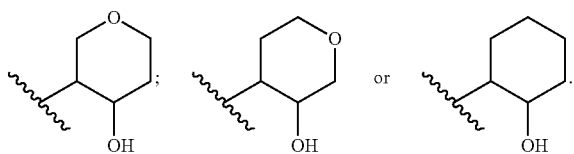 [SMILES: *C1COCCC1O ; *C1CCOCC1O ; *C1CCCCC1O]

$R^1$ is further more preferably

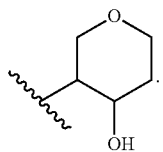

In another embodiment of the present invention, $R^1$ is preferably

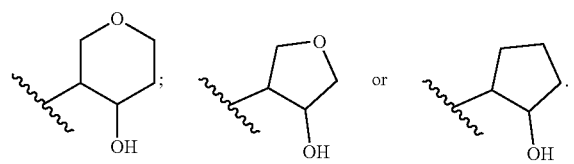 [SMILES: *C1COCCC1O ; *C1COCC1O ; *C1CCCC1O]

In another embodiment of the present invention, $R^1$ is preferably an optionally substituted 3- to 8-membered monocyclic non-aromatic heterocyclic group.

In another embodiment of the present invention, $R^1$ is preferably

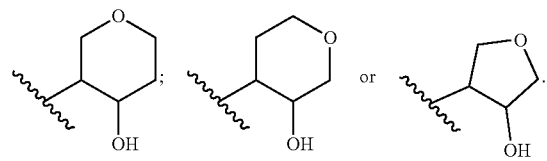 [SMILES: *C1COCCC1O ; *C1CCOCC1O ; *C1COCC1O]

$R^1$ is more preferably

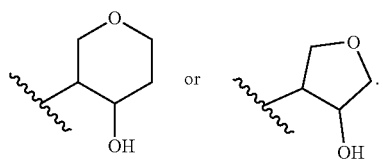 [SMILES: *C1COCCC1O ; *C1COCC1O]

$R^2$ is a fluorine atom or an optionally substituted $C_{1-6}$ alkoxy group.

As the substituent of the "optionally substituted $C_{1-6}$ alkoxy group" for $R^2$, a halogen atom (e.g., fluorine atom), a $C_{3-10}$ cycloalkyl group (e.g., cyclopropyl) and the like can be mentioned.

$R^2$ is preferably a fluorine atom, or a $C_{1-6}$ alkoxy group (e.g., methoxy, ethoxy, isopropoxy) optionally substituted by 1 to 3 substituents selected from a halogen atom (e.g., fluorine atom) and a $C_{3-10}$ cycloalkyl group (e.g., cyclopropyl). $R^2$ is more preferably a fluorine atom or a $C_{1-6}$ alkoxy group (e.g., methoxy).

In another embodiment of the present invention, $R^2$ is preferably an optionally substituted $C_{1-6}$ alkoxy group. $R^2$ is more preferably a $C_{1-6}$ alkoxy group (e.g., methoxy, ethoxy, isopropoxy) optionally substituted by 1 to 3 substituents selected from a halogen atom (e.g., fluorine atom) and a $C_{3-10}$ cycloalkyl group (e.g., cyclopropyl). $R^2$ is further preferably a $C_{1-6}$ alkoxy group (e.g., methoxy).

In another embodiment of the present invention, $R^2$ is preferably a fluorine atom.

$R^3$ is a hydrogen atom, a halogen atom, a cyano group, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted $C_{3-10}$ cycloalkyl group or an optionally substituted $C_{3-10}$ cycloalkyloxy group.

$R^3$ is preferably a hydrogen atom, a halogen atom (e.g., fluorine atom, chlorine atom) or an optionally substituted $C_{1-6}$ alkyl group (e.g., methyl). $R^3$ is more preferably a hydrogen atom, a halogen atom (e.g., fluorine atom, chlorine atom) or a $C_{1-6}$ alkyl group (e.g., methyl). $R^3$ is further preferably a halogen atom (e.g., fluorine atom, chlorine atom) or a $C_{1-6}$ alkyl group (e.g., methyl). $R^3$ is further more preferably a $C_{1-6}$ alkyl group (e.g., methyl).

$R^4$ is a hydrogen atom, a halogen atom, a cyano group, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted $C_{3-10}$ cycloalkyl group or an optionally substituted $C_{3-10}$ cycloalkyloxy group.

$R^4$ is preferably a cyano group or an optionally substituted $C_{1-6}$ alkyl group (e.g., methyl). $R^4$ is more preferably a cyano group or a $C_{1-6}$ alkyl group (e.g., methyl). $R^4$ is further preferably a $C_{1-6}$ alkyl group (e.g., methyl).

$R^5$ and $R^6$ are each independently a hydrogen atom or a halogen atom.

$R^5$ and $R^6$ are preferably both hydrogen atoms.

Ring A is a further optionally substituted benzene ring, or a further optionally substituted 6-membered aromatic heterocycle.

As the substituent of the "further optionally substituted benzene ring" for ring A, an optionally substituted 5- to 14-membered aromatic heterocyclic group (e.g., pyrazolyl, oxazolyl, thiazolyl, triazolyl) and the like can be mentioned.

As the substituent of the "further optionally substituted 6-membered aromatic heterocycle" for ring A, an optionally substituted $C_{1-6}$ alkyl group (e.g., methyl), an optionally substituted 5- to 14-membered aromatic heterocyclic group (e.g., pyrazolyl) and the like can be mentioned.

Ring A is preferably a benzene ring optionally further substituted by 1 to 3 substituents selected from an optionally substituted 5- to 14-membered aromatic heterocyclic group (e.g., pyrazolyl, oxazolyl, thiazolyl, triazolyl), or a 6-membered aromatic heterocycle (e.g., a pyridine ring) optionally further substituted by 1 to 3 substituents selected from an optionally substituted $C_{1-6}$ alkyl group (e.g., methyl) and an optionally substituted 5- to 14-membered aromatic heterocyclic group (e.g., pyrazolyl). Ring A is more preferably a benzene ring optionally further substituted by 1 to 3 substituents selected from a 5- to 14-membered aromatic heterocyclic group (e.g., pyrazolyl, oxazolyl, thiazolyl, triazolyl) optionally substituted by 1 to 3 $C_{1-6}$ alkyl groups (e.g., methyl), or a 6-membered aromatic heterocycle (e.g., a pyridine ring) optionally further substituted by 1 to 3 substituents selected from a $C_{1-6}$ alkyl group (e.g., methyl) and a 5- to 14-membered aromatic heterocyclic group (e.g., pyrazolyl) optionally substituted by 1 to 3 $C_{1-6}$ alkyl groups (e.g., methyl). Ring A is further preferably a benzene ring optionally further substituted by 1 to 3 substituents selected from 5- to 14-membered aromatic heterocyclic group (preferably, 5- or 6-membered monocyclic aromatic heterocyclic group) (e.g., pyrazolyl, thiazolyl, triazolyl) optionally substituted by 1 to 3 $C_{1-6}$ alkyl groups (e.g., methyl). Ring A is further more preferably a benzene ring further substituted by 1 to 3 substituents selected from a 5- or 6-membered monocyclic aromatic heterocyclic group (e.g., pyrazolyl, triazolyl). Ring A is particularly preferably a benzene ring further substituted by 1 to 3 substituents selected from pyrazolyl and triazolyl.

As a preferable embodiment of compound (I), the following compound can be mentioned.

[Compound I-1-1]
Compound (I) wherein
$R^1$ is a $C_{1-6}$ alkyl group (e.g., methyl) substituted by 1 to 3 substituents selected from an optionally substituted non-aromatic heterocyclic group (e.g., tetrahydrofuranyl),
an optionally substituted $C_{3-10}$ cycloalkyl group (e.g., cyclopentyl, cyclohexyl), or
an optionally substituted non-aromatic heterocyclic group (e.g., tetrahydrofuranyl, tetrahydropyranyl);
$R^2$ is a fluorine atom, or an optionally substituted $C_{1-6}$ alkoxy group (e.g., methoxy, ethoxy, isopropoxy);
$R^3$ is a hydrogen atom, a halogen atom (e.g., fluorine atom, chlorine atom) or an optionally substituted $C_{1-6}$ alkyl group (e.g., methyl);
$R^4$ is an optionally substituted $C_{1-6}$ alkyl group (e.g., methyl);
$R^5$ and $R^6$ are both hydrogen atoms; and
ring A is a benzene ring optionally further substituted by 1 to 3 substituents selected from an optionally substituted 5- to 14-membered aromatic heterocyclic group (e.g., pyrazolyl, oxazolyl, thiazolyl, triazolyl), or
a 6-membered aromatic heterocycle (e.g., a pyridine ring) optionally further substituted by 1 to 3 substituents selected from an optionally substituted $C_{1-6}$ alkyl group (e.g., methyl) and an optionally substituted 5- to 14-membered aromatic heterocyclic group (e.g., pyrazolyl).

[Compound I-1-2]
Compound (I) wherein
$R^1$ is a $C_{1-6}$ alkyl group (e.g., methyl) substituted by 1 to 3 substituents selected from an optionally substituted non-aromatic heterocyclic group (e.g., tetrahydrofuranyl),
an optionally substituted non-crosslinked $C_{3-10}$ cycloalkyl group (e.g., cyclopentyl, cyclohexyl), or
an optionally substituted 3- to 8-membered monocyclic non-aromatic heterocyclic group (e.g., tetrahydrofuranyl, tetrahydropyranyl);
$R^2$ is a fluorine atom, or an optionally substituted $C_{1-6}$ alkoxy group (e.g., methoxy, ethoxy, isopropoxy);
$R^3$ is a hydrogen atom, a halogen atom (e.g., fluorine atom, chlorine atom) or an optionally substituted $C_{1-6}$ alkyl group (e.g., methyl);
$R^4$ is an optionally substituted $C_{1-6}$ alkyl group (e.g., methyl);
$R^5$ and $R^6$ are both hydrogen atoms; and
ring A is a benzene ring optionally further substituted by 1 to 3 substituents selected from an optionally substituted 5- to 14-membered aromatic heterocyclic group (e.g., pyrazolyl, oxazolyl, thiazolyl, triazolyl), or
a 6-membered aromatic heterocycle (e.g., a pyridine ring) optionally further substituted by 1 to 3 substituents selected from an optionally substituted $C_{1-6}$ alkyl group (e.g., methyl) and an optionally substituted 5- to 14-membered aromatic heterocyclic group (e.g., pyrazolyl).

[Compound I-1-1A]
Compound (I) wherein
$R^1$ is a $C_{1-6}$ alkyl group (e.g., methyl) substituted by 1 to 3 substituents selected from an optionally substituted non-aromatic heterocyclic group (e.g., tetrahydrofuranyl),
an optionally substituted $C_{3-10}$ cycloalkyl group (e.g., cyclopentyl, cyclohexyl), or
an optionally substituted non-aromatic heterocyclic group (e.g., tetrahydrofuranyl, tetrahydropyranyl);
$R^2$ is a fluorine atom, or an optionally substituted $C_{1-6}$ alkoxy group (e.g., methoxy, ethoxy, isopropoxy);
$R^3$ is a hydrogen atom, a halogen atom (e.g., fluorine atom, chlorine atom) or an optionally substituted $C_{1-6}$ alkyl group (e.g., methyl);
$R^4$ is a cyano group or an optionally substituted $C_{1-6}$ alkyl group (e.g., methyl);
$R^5$ and $R^6$ are both hydrogen atoms; and
ring A is a benzene ring optionally further substituted by 1 to 3 substituents selected from an optionally substituted 5- to 14-membered aromatic heterocyclic group (e.g., pyrazolyl, oxazolyl, thiazolyl, triazolyl), or
a 6-membered aromatic heterocycle (e.g., a pyridine ring) optionally further substituted by 1 to 3 substituents selected from an optionally substituted $C_{1-6}$ alkyl group (e.g., methyl) and an optionally substituted 5- to 14-membered aromatic heterocyclic group (e.g., pyrazolyl).

[Compound I-1-2A]
The aforementioned [compound I-1-1A] wherein
$R^1$ is a $C_{1-6}$ alkyl group (e.g., methyl) substituted by 1 to 3 substituents selected from an optionally substituted non-aromatic heterocyclic group (e.g., tetrahydrofuranyl),
an optionally substituted non-crosslinked $C_{3-10}$ cycloalkyl group (e.g., cyclopentyl, cyclohexyl), or
an optionally substituted 3- to 8-membered monocyclic non-aromatic heterocyclic group (e.g., tetrahydrofuranyl, tetrahydropyranyl).

[Compound I-1-1B]
Compound (I), the aforementioned [compound I-1-1], the aforementioned [compound I-1-2], the aforementioned [compound I-1-1A], or the aforementioned [compound I-1-2A] wherein
$R^2$ is an optionally substituted $C_{1-6}$ alkoxy group (e.g., methoxy, ethoxy, isopropoxy).

[Compound I-1-2B]
Compound (I), the aforementioned [compound I-1-1], the aforementioned [compound I-1-2], the aforementioned [compound I-1-1A], or the aforementioned [compound I-1-2A] wherein
$R^2$ is a fluorine atom.

[Compound I-2-1]
Compound (I) wherein
$R^1$ is (A) a $C_{1-6}$ alkyl group (e.g., methyl) substituted by 1 to 3 substituents selected from a non-aromatic heterocyclic group (e.g., tetrahydrofuranyl), (B) a $C_{3-10}$ cycloalkyl group (e.g., cyclopentyl, cyclohexyl) optionally substituted by a hydroxy group, or (C) a non-aromatic heterocyclic group (e.g., tetrahydrofuranyl, tetrahydropyranyl) optionally substituted by a hydroxy group;
$R^2$ is
a fluorine atom, or
a $C_{1-6}$ alkoxy group (e.g., methoxy, ethoxy, isopropoxy) optionally substituted by 1 to 3 substituents selected from a halogen atom (e.g., fluorine atom) and a $C_{3-10}$ cycloalkyl group (e.g., cyclopropyl);
$R^3$ is a hydrogen atom, a halogen atom (e.g., fluorine atom, chlorine atom) or a $C_{1-6}$ alkyl group (e.g., methyl);

$R^4$ is a $C_{1-6}$ alkyl group (e.g., methyl);
$R^5$ and $R^6$ are both hydrogen atoms; and
ring A is a benzene ring optionally further substituted by 1 to 3 substituents selected from a 5- to 14-membered aromatic heterocyclic group (e.g., pyrazolyl, oxazolyl, thiazolyl, triazolyl) optionally substituted by 1 to 3 $C_{1-6}$ alkyl groups (e.g., methyl), or
a 6-membered aromatic heterocycle (e.g., a pyridine ring) optionally further substituted by 1 to 3 substituents selected from a $C_{1-6}$ alkyl group (e.g., methyl) and a 5- to 14-membered aromatic heterocyclic group (e.g., pyrazolyl) optionally substituted by 1 to 3 $C_{1-6}$ alkyl groups (e.g., methyl).

[Compound I-2-2]
Compound (I) wherein
$R^1$ is (A) a $C_{1-6}$ alkyl group (e.g., methyl) substituted by 1 to 3 substituents selected from a non-aromatic heterocyclic group (e.g., tetrahydrofuranyl), (B) a non-crosslinked $C_{3-10}$ cycloalkyl group (e.g., cyclopentyl, cyclohexyl) optionally substituted by a hydroxy group, or (C) a 3- to 8-membered monocyclic non-aromatic heterocyclic group (e.g., tetrahydrofuranyl, tetrahydropyranyl) optionally substituted by a hydroxy group;
$R^2$ is
a fluorine atom, or
a $C_{1-6}$ alkoxy group (e.g., methoxy, ethoxy, isopropoxy) optionally substituted by 1 to 3 substituents selected from a halogen atom (e.g., fluorine atom) and a $C_{3-10}$ cycloalkyl group (e.g., cyclopropyl);
$R^3$ is a hydrogen atom, a halogen atom (e.g., fluorine atom, chlorine atom) or a $C_{1-6}$ alkyl group (e.g., methyl);
$R^4$ is a $C_{1-6}$ alkyl group (e.g., methyl);
$R^5$ and $R^6$ are both hydrogen atoms; and
ring A is a benzene ring optionally further substituted by 1 to 3 substituents selected from a 5- to 14-membered aromatic heterocyclic group (e.g., pyrazolyl, oxazolyl, thiazolyl, triazolyl) optionally substituted by 1 to 3 $C_{1-6}$ alkyl groups (e.g., methyl), or
a 6-membered aromatic heterocycle (e.g., a pyridine ring) optionally further substituted by 1 to 3 substituents selected from a $C_{1-6}$ alkyl group (e.g., methyl) and a 5- to 14-membered aromatic heterocyclic group (e.g., pyrazolyl) optionally substituted by 1 to 3 $C_{1-6}$ alkyl groups (e.g., methyl).

[Compound I-2-1A]
Compound (I) wherein
$R^1$ is (A) a $C_{1-6}$ alkyl group (e.g., methyl) substituted by 1 to 3 substituents selected from a non-aromatic heterocyclic group (e.g., tetrahydrofuranyl), (B) a $C_{3-10}$ cycloalkyl group (e.g., cyclopentyl, cyclohexyl) optionally substituted by a hydroxy group, or (C) a non-aromatic heterocyclic group (e.g., tetrahydrofuranyl, tetrahydropyranyl) optionally substituted by a hydroxy group;
$R^2$ is a fluorine atom, or
a $C_{1-6}$ alkoxy group (e.g., methoxy, ethoxy, isopropoxy) optionally substituted by 1 to 3 substituents selected from a halogen atom (e.g., fluorine atom) and a $C_{3-10}$ cycloalkyl group (e.g., cyclopropyl);
$R^3$ is a hydrogen atom, a halogen atom (e.g., fluorine atom, chlorine atom) or a $C_{1-6}$ alkyl group (e.g., methyl);
$R^4$ is a cyano group or a $C_{1-6}$ alkyl group (e.g., methyl);
$R^5$ and $R^6$ are both hydrogen atoms; and
ring A is a benzene ring optionally further substituted by 1 to 3 substituents selected from a 5- to 14-membered aromatic heterocyclic group (e.g., pyrazolyl, oxazolyl, thiazolyl, triazolyl) optionally substituted by 1 to 3 $C_{1-6}$ alkyl groups (e.g., methyl), or
a 6-membered aromatic heterocycle (e.g., a pyridine ring) optionally further substituted by 1 to 3 substituents selected from a $C_{1-6}$ alkyl group (e.g., methyl) and a 5- to 14-membered aromatic heterocyclic group (e.g., pyrazolyl) optionally substituted by 1 to 3 $C_{1-6}$ alkyl groups (e.g., methyl).

[Compound I-2-2A]
The aforementioned [compound I-2-1A] wherein
$R^1$ is (A) a $C_{1-6}$ alkyl group (e.g., methyl) substituted by 1 to 3 substituents selected from a non-aromatic heterocyclic group (e.g., tetrahydrofuranyl), (B) a non-crosslinked $C_{3-10}$ cycloalkyl group (e.g., cyclopentyl, cyclohexyl) optionally substituted by a hydroxy group, or (C) a 3- to 8-membered monocyclic non-aromatic heterocyclic group (e.g., tetrahydrofuranyl, tetrahydropyranyl) optionally substituted by a hydroxy group.

[Compound I-2-3A]
The aforementioned [compound I-2-1A] wherein
$R^1$ is

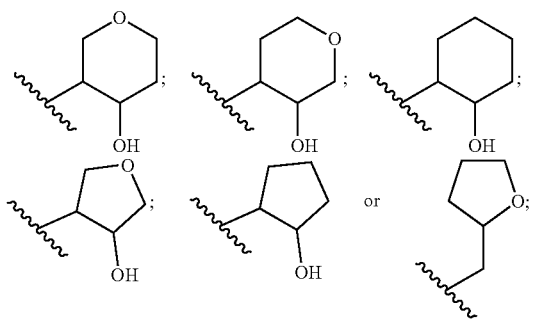

$R^3$ is a halogen atom (e.g., fluorine atom, chlorine atom) or a $C_{1-6}$ alkyl group (e.g., methyl).

[Compound I-2-4A]
The aforementioned [compound I-2-3A] wherein
$R^1$ is

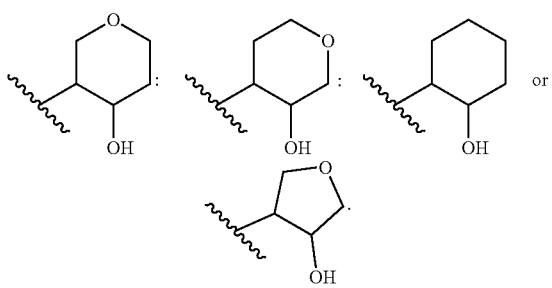

[Compound I-2-5A]
The aforementioned [compound I-2-3A] wherein
$R^1$ is

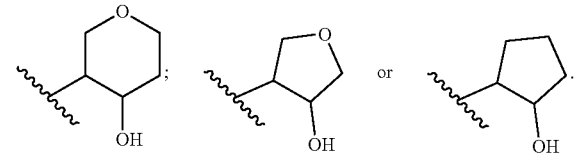 [SMILES: *C1COCCC1O ; *C1COCC1O ; *C1CCCC1O]

[Compound I-2-1B]
The aforementioned [compound I-2-1], the aforementioned [compound I-2-2], the aforementioned [compound I-2-1A], the aforementioned [compound I-2-2A], the aforementioned [compound I-2-3A], the aforementioned [compound I-2-4A] or the aforementioned [compound I-2-5A] wherein
$R^2$ is a $C_{1-6}$ alkoxy group (e.g., methoxy, ethoxy, isopropoxy) optionally substituted by 1 to 3 substituents selected from a halogen atom (e.g., fluorine atom) and a $C_{3-10}$ cycloalkyl group (e.g., cyclopropyl).
[Compound I-2-2B]
The aforementioned [compound I-2-1], the aforementioned [compound I-2-2], the aforementioned [compound I-2-1A], the aforementioned [compound I-2-2A], the aforementioned [compound I-2-3A], the aforementioned [compound I-2-4A] or the aforementioned [compound I-2-5A] wherein
$R^2$ is a fluorine atom.
[Compound I-3-1]
Compound (I) wherein
$R^1$ is a $C_{3-10}$ cycloalkyl group (e.g., cyclohexyl) optionally substituted by a hydroxy group, or
a non-aromatic heterocyclic group (e.g., tetrahydropyranyl) optionally substituted by a hydroxy group;
$R^2$ is a fluorine atom, or a $C_{1-6}$ alkoxy group (e.g., methoxy);
$R^3$ is a halogen atom (e.g., fluorine atom) or a $C_{1-6}$ alkyl group (e.g., methyl);
$R^4$ is a $C_{1-6}$ alkyl group (e.g., methyl);
$R^5$ and $R^6$ are both hydrogen atoms; and
ring A is a benzene ring optionally further substituted by 1 to 3 substituents selected from a 5- to 14-membered aromatic heterocyclic group (e.g., pyrazolyl, thiazolyl, triazolyl) optionally substituted by 1 to 3 $C_{1-6}$ alkyl groups (e.g., methyl).
[Compound I-3-2]
Compound (I) wherein
$R^1$ is a non-crosslinked $C_{3-10}$ cycloalkyl group (e.g., cyclohexyl) optionally substituted by a hydroxy group or a 3- to 8-membered monocyclic non-aromatic heterocyclic group (e.g., tetrahydropyranyl) optionally substituted by a hydroxy group;
$R^2$ is a fluorine atom, or a $C_{1-6}$ alkoxy group (e.g., methoxy);
$R^3$ is a halogen atom (e.g., fluorine atom) or a $C_{1-6}$ alkyl group (e.g., methyl);
$R^4$ is a $C_{1-6}$ alkyl group (e.g., methyl);
$R^5$ and $R^6$ are both hydrogen atoms; and
ring A is a benzene ring optionally further substituted by 1 to 3 substituents selected from a 5- to 14-membered aromatic heterocyclic group (e.g., pyrazolyl, thiazolyl, triazolyl) optionally substituted by 1 to 3 $C_{1-6}$ alkyl groups (e.g., methyl).
[Compound I-3-1A]
The aforementioned [compound I-3-2] wherein
$R^1$ is

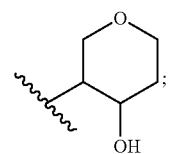 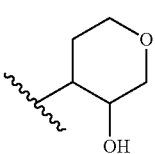 or 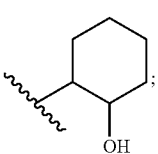

and
ring A is a benzene ring optionally further substituted by 1 to 3 substituents selected from a 5- or 6-membered monocyclic aromatic heterocyclic group (e.g., pyrazolyl, thiazolyl, triazolyl) optionally substituted by 1 to 3 $C_{1-6}$ alkyl groups (e.g., methyl).
[Compound I-3-2A]
The aforementioned [compound I-3-2] wherein
$R^1$ is

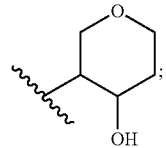

$R^3$ is a $C_{1-6}$ alkyl group (e.g., methyl); and
ring A is a benzene ring further substituted by 1 to 3 substituents selected from a 5- or 6-membered monocyclic aromatic heterocyclic group (e.g., pyrazolyl, triazolyl).
[Compound I-3-3A]
The aforementioned [compound I-3-2A] wherein ring A is a benzene ring further substituted by 1 to 3 substituents selected from pyrazolyl and triazolyl.
[Compound I-4]
Compound (I) wherein
$R^1$ is

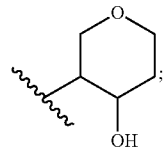 [SMILES: *C1COCCC1O]

$R^2$ is a fluorine atom or a $C_{1-6}$ alkoxy group (e.g., methoxy);
$R^3$ is a $C_{1-6}$ alkyl group (e.g., methyl);
$R^4$ is a $C_{1-6}$ alkyl group (e.g., methyl);
$R^5$ and $R^6$ are both hydrogen atoms; and
ring A is a benzene ring further substituted by a 5- or 6-membered monocyclic aromatic heterocyclic group (e.g., pyrazolyl, triazolyl) optionally substituted by one $C_{1-6}$ alkyl group (e.g., methyl).
[Compound I-5]
The aforementioned [compound I-3-1], the aforementioned [compound I-3-2], the aforementioned [compound I-3-1A], the aforementioned [compound I-3-2A], the aforementioned [compound I-3-3A] or the aforementioned [compound I-4] wherein
$R^2$ is a $C_{1-6}$ alkoxy group (e.g., methoxy).
[Compound I-6]
The aforementioned [compound I-3-1], the aforementioned [compound I-3-2], the aforementioned [compound I-3-1A], the aforementioned [compound I-3-2A], the aforementioned [compound I-3-3A] or the aforementioned [compound I-4] wherein
$R^2$ is a fluorine atom.
Specific examples of compound (I) include the compounds of Examples 1-47, and
N-(trans-2-hydroxycyclohexyl)-2-methoxy-3,4-dimethyl-5-(4-(1-methyl-1H-1,2,3-triazol-4-yl)benzyl)benzamide (optical isomer, short retention time) (Example 10),
2-fluoro-N-((3S,4S)-4-hydroxytetrahydro-2H-pyran-3-yl)-3,4-dimethyl-5-(4-(1H-pyrazol-1-yl)benzyl)benzamide (Example 12), N-((3S,4S)-4-hydroxytetrahydro-2H-pyran-3-yl)-2-methoxy-3,4-dimethyl-5-(4-(1-methyl-1H-1,2,3-triazol-4-yl)benzyl)benzamide (Example 13), N-((1S,2S)-2-hydroxycyclohexyl)-2-methoxy-3,4-dimethyl-5-(4-(1H-1,2,3-triazol-1-yl)benzyl)benzamide (Example 14), 1,5-anhydro-2,3-dideoxy-3-((2-methoxy-3,4-dimethyl-5-(4-(1-methyl-1H-1,2,3-triazol-4-yl)benzyl)benzoyl)amino)-L-threo-pentitol (Example 24), 1,5-anhydro-2,4-dideoxy-2-((2,3-difluoro-4-methyl-5-(4-(1H-pyrazol-1-yl)benzyl)benzoyl)amino)-L-threo-pentitol (Example 25), 1,5-anhydro-2,4-dideoxy-2-((2-methoxy-3,4-dimethyl-5-(4-(1-methyl-1H-pyrazol-3-yl)benzyl)benzoyl)amino)-L-threo-pentitol (Example 26), and 1,5-anhydro-2,4-dideoxy-2-((2-fluoro-3,4-dimethyl-5-(4-(1,3-thiazol-4-yl)benzyl)benzoyl)amino)-L-threo-pentitol (Example 32)

are preferable.

When compound (I) is in a form of a salt, examples of such salt include salts with inorganic base, an ammonium salt, is salts with organic base, salts with inorganic acid, salts with organic acid, salts with basic or acidic amino acid, and the like.

Preferable examples of the salt with inorganic base include alkali metal salts such as sodium salt, potassium salt and the like; alkaline earth metal salts such as calcium salt, magnesium salt, barium salt and the like; an aluminum salt, and the like.

Preferable examples of the salt with organic base include salts with trimethylamine, triethylamine, pyridine, picoline, ethanolamine, diethanolamine, triethanolamine, dicyclohexylamine, N,N'-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like.

Preferable examples of the salt with acidic amino acid include salts with aspartic acid, glutamic acid and the like.

Among these salts, a pharmaceutically acceptable salt is preferable. When a compound has a basic functional group, examples of a preferable pharmaceutically acceptable salt include salts with inorganic acid such as hydrochloric acid, hydrobromic acid, nitric acid, sulfuric acid, phosphoric acid and the like, and salts with organic acid such as acetic acid, phthalic acid, fumaric acid, oxalic acid, tartaric acid, maleic acid, citric acid, succinic acid, methanesulfonic acid, p-toluenesulfonic acid and the like. In addition, when a compound has an acidic functional group, examples thereof include inorganic salts such as alkali metal salts (e.g., sodium salt, potassium salt etc.), alkaline earth metal salts (e.g., calcium salt, magnesium salt, barium salt etc.) and the like, ammonium salt and the like.

Compound (I) may be a crystal, and both a single crystal and crystal mixtures are encompassed in the compound (I). The crystal can be produced by performing crystallization by a crystallization method known per se.

Compound (I) may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, solubility, stability etc.). The cocrystal and cocrystal salt can be produced by cocrystallization method known per se.

Compound (I) encompasses solvates (e.g., hydrate) and non-solvates within the scope thereof. Compound (I) may be a compound labeled or substituted with an isotope (e.g., $^2H$, $^3H$, $^{11}C$, $^{14}C$, $^{18}F$, $^{35}S$, $^{125}I$). A compound labeled with or substituted by an isotope can be used, for example, as a tracer used for Positron Emission Tomography (PET) (PET tracer), and is useful in the field of medical diagnosis and the like.

When compound (I) has an asymmetric center, isomers such as enantiomer, diastereomer and the like may be present. Such isomers and a mixture thereof are all encompassed within the scope of compound (I). When an isomer is formed due to the conformation or tautomerism, such isomers and a mixture thereof are all encompassed in compound (I).

The production methods of the compound of the present invention are explained below.

The starting materials and reagents used in each step in the following production method, and the obtained compounds each may form a salt. Examples of the salt include those similar to the aforementioned salts of the compound (I) and the like.

When the compound obtained in each step is a free compound, it can be converted to a desired salt by a method known per se. Conversely, when the compound obtained in each step is a salt, it can be converted to a free form or a desired other kind of salt by a method known per se.

The compound obtained in each step can also be used for the next reaction as a reaction mixture thereof or after obtaining a crude product thereof. Alternatively, the compound obtained in each step can be isolated and/or purified from the reaction mixture by a separation means such as concentration, crystallization, recrystallization, distillation, solvent extraction, fractionation, chromatography and the like according to a conventional method.

When the starting materials and reagent compounds of each step are commercially available, the commercially available products can be used as they are.

In the reaction of each step, while the reaction time varies depending on the reagents and solvents to be used, unless otherwise specified, it is generally 1 min to 48 hr, preferably 10 min to 8 hr.

In the reaction of each step, while the reaction temperature varies depending on the reagents and solvents to be used, unless otherwise specified, it is generally −78° C. to 300° C., preferably −78° C. to 150° C.

In the reaction of each step, while the pressure varies depending on the reagents and solvents to be used, unless otherwise specified, it is generally 1 atm-20 atm, preferably 1 atm-3 atm.

In the reaction of each step, for example, microwave synthesizers such as Initiator manufactured by Biotage and the like are sometimes used. While the reaction temperature varies depending on the reagents and solvents to be used, unless otherwise specified, it is generally room temperature −300° C., preferably 50° C.-250° C. While the reaction time varies depending on the reagents and solvents to be used, unless otherwise specified, it is generally 1 min to 48 hr, preferably 1 min to 8 hr.

In the reaction of each step, unless otherwise specified, a reagent is used in 0.5 equivalent-20 equivalents, preferably 0.8 equivalent-5 equivalents, relative to the substrate. When a reagent is used as a catalyst, the reagent is used in 0.001 equivalent-1 equivalent, preferably 0.01 equivalent-0.2 equivalent, relative to the substrate. When the reagent is also a reaction solvent, the reagent is used in a solvent amount.

In the reaction of each step, unless otherwise specified, it is performed without solvent or by dissolving or suspending in a suitable solvent. Specific examples of the solvent include those described in Examples and the following.
alcohols: methanol, ethanol, tert-butyl alcohol, 2-methoxyethanol and the like;
ethers: diethyl ether, diphenyl ether, tetrahydrofuran, 1,2-dimethoxyethane and the like;
aromatic hydrocarbons: chlorobenzene, toluene, xylene and the like;
saturated hydrocarbons: cyclohexane, hexane and the like;
amides: N,N-dimethylformamide, N-methylpyrrolidone and the like;
halogenated hydrocarbons: dichloromethane, carbon tetrachloride and the like;
nitriles: acetonitrile and the like;
sulfoxides: dimethyl sulfoxide and the like;
aromatic organic bases: pyridine and the like;
acid anhydrides: acetic anhydride and the like;
organic acids: formic acid, acetic acid, trifluoroacetic acid and the like;
inorganic acids: hydrochloric acid, sulfuric acid and the like;
esters: ethyl acetate and the like;
ketones: acetone, methyl ethyl ketone and the like; and water.

Two or more kinds of the above-mentioned solvents may be used by mixing at an appropriate ratio.

When a base is used in the reaction of each step, for example, bases shown below or those described in Examples are used.
inorganic bases: sodium hydroxide, magnesium hydroxide, sodium carbonate, calcium carbonate, sodium hydrogen carbonate and the like;
organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;
metal alkoxides: sodium ethoxide, potassium tert-butoxide and the like;
alkali metal hydrides: sodium hydride and the like; metal amides: sodium amide, lithium diisopropyl amide, lithium hexamethyl disilazide and the like; and
organic lithiums: n-butyllithium and the like.

When an acid or acidic catalyst is used in the reaction of each step, for example, acids and acidic catalysts shown below or those described in Examples are used.
inorganic acids: hydrochloric acid, sulfuric acid, nitric acid, hydrobromic acid, phosphoric acid and the like;
organic acids: acetic acid, trifluoroacetic acid, citric acid, p-toluenesulfonic acid, 10-camphorsulfonic acid and the like; and
Lewis acids: boron trifluoride diethyl ether complex, zinc iodide, anhydrous aluminum chloride, anhydrous zinc chloride, anhydrous iron chloride and the like.

Unless otherwise specified, the reaction of each step is performed according to a method known per se, for example, the methods described in Jikken Kagaku Kouza 5th edition, vol. 13-vol. 19 (The Chemical Society of Japan ed.); Shinjikken Kagaku Kouza (Courses in Experimental Chemistry), vol. 14-vol. 15 (The Chemical Society of Japan ed.); Fine Organic Chemistry rev. 2nd edition (L. F. Tietze, Th. Eicher, NANKODO); rev. Organic Name Reactions, Their Mechanism and Essence (Hideo Togo, Kodansha); ORGANIC SYNTHESES Collective Volume I-VII (John Wiley & Sons Inc); Modern Organic Synthesis in the Laboratory, A Collection of Standard Experimental Procedures (Jie Jack Li, OXFORD UNIVERSITY); Comprehensive Heterocyclic Chemistry III, Vol. 1-Vol. 14 (Elsevier Japan KK); Strategic Applications of Named Reactions in Organic Synthesis (translation supervisor Kiyoshi Tomioka, KAGAKUDOJIN); Comprehensive Organic Transformations (VCH Publishers Inc.), 1989 and the like, or the methods described in the Examples.

In each step, protection or deprotection reaction of a functional group is performed by the method known per se, for example, the methods described in "Protective Groups in Organic Synthesis, 4th Ed." (Theodora W. Greene, Peter G. M. Wuts) Wiley-Interscience, 2007; "Protecting Groups 3rd Ed." (P. J. Kocienski) Thieme, 2004 and the like, or the methods described in the Examples.

Examples of the protecting group of the hydroxyl group of alcohol and the like and a phenolic hydroxyl group include ether protecting groups such as methoxymethyl ether, benzyl ether, tert-butyldimethylsilyl ether, tetrahydropyranyl ether and the like; carboxylate ester protecting groups such as acetate ester and the like; sulfonate ester protecting groups such as methanesulfonate ester and the like; carbonate ester protecting groups such as tert-butylcarbonate and the like, and the like.

Examples of the protecting group of the carbonyl group of aldehyde include acetal protecting groups such as dimethyl acetal and the like; cyclic acetal protecting groups such as 1,3-dioxane and the like, and the like.

Examples of the protecting group of the carbonyl group of ketone include ketal protecting groups such as dimethyl ketal and the like; cyclic ketal protecting groups such as 1,3-dioxane and the like; oxime protecting groups such as O-methyloxime and the like; hydrazone protecting groups such as N,N-dimethylhydrazone and the like, and the like.

Examples of the carboxyl protecting group include ester protecting groups such as methyl ester and the like; amide protecting groups such as N,N-dimethylamide and the like, and the like.

Examples of the thiol protecting group include ether protecting groups such as benzyl thioether and the like; ester protecting groups such as thioacetate ester, thiocarbonate, thiocarbamate and the like, and the like.

Examples of the protecting group of an amino group and an aromatic heterocycle such as imidazole, pyrrole, indole and the like include carbamate protecting groups such as benzyl carbamate and the like; amide protecting groups such as acetamide and the like; alkylamine protecting groups such as N-triphenylmethylamine and the like, sulfonamide protecting groups such as methanesulfonamide and the like, and the like.

The protecting group can be removed by a method known per se, for example, a method using acid, base, ultraviolet light, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide), a reduction method and the like.

When a reduction reaction is performed in each step, examples of the reducing agent to be used include metal hydrides such as lithium aluminum hydride, sodium triacetoxyborohydride, sodium cyanoborohydride, diisobutylaluminum hydride (DIBAL-H), sodium borohydride, tetramethylammonium triacetoxyborohydride and the like; boranes such as borane tetrahydrofuran complex and the like; Raney nickel; Raney cobalt; hydrogen; formic acid; triethylsilane and the like. When a carbon-carbon double bond or triple bond is reduced, a method using a catalyst such as palladium-carbon, Lindlar catalyst and the like is used.

When an oxidation reaction is performed in each step, examples of an oxidant to be used include peracids such as m-chloroperbenzoic acid (mCPBA), hydrogen peroxide, tert-butyl hydroperoxide and the like; perchlorates such as tetrabutylammonium perchlorate and the like; chlorates such as sodium chlorate and the like; chlorites such as sodium chlorite and the like; periodic acids such as sodium periodate and the like; high valent iodine reagents such as iodosylbenzene and the like; reagents containing manganese such as manganese dioxide, potassium permanganate and the like; leads such as lead tetraacetate and the like; reagents containing chrome such as pyridinium chlorochromate (PCC), pyridinium dichromate (PDC), Jones reagent and the like; halogen compounds such as N-bromosuccinimide (NBS) and the like; oxygen; ozone; sulfur trioxide pyridine complex; osmium tetraoxide; selenium dioxide; 2,3-dichloro-5, 6-dicyano-1,4-benzoquinone (DDQ) and the like.

When a radical cyclization reaction is performed in each step, examples of the radical initiator to be used include azo compounds such as azobisisobutyronitrile (AIBN) and the like; water-soluble radical initiators such as 4,4'-azobis-4-cyanopentanoic acid (ACPA) and the like; triethylboron in the presence of air or oxygen; benzoyl peroxide and the like. In addition, examples of the radical reaction agent to be used include tributylstannane, tristrimethylsilylsilane, 1,1,2,2-tetraphenyldisilane, diphenylsilane, samarium iodide and the like.

When the Wittig reaction is performed in each step, examples of the Wittig reagent to be used include alkylidenephosphoranes and the like. Alkylidenephosphoranes can be prepared by a method known per se, for example, by reacting a phosphonium salt with a strong base.

When the Horner-Emmons reaction is performed in each step, examples of the reagent to be used include phosphonoacetic acid esters such as methyl dimethylphosphonoacetate, ethyl diethylphosphonoacetate and the like; and bases such as alkali metal hydrides, organic lithiums and the like.

When the Friedel-Crafts reaction is performed in each step, examples of the reagent to be used include a combination of Lewis acid and acid chloride or a combination of Lewis acid and an alkylating agent (e.g., alkyl halides, alcohol, olefins and the like). Alternatively, an organic acid and an inorganic acid can also be used instead of the Lewis acid, and acid anhydride such as acetic anhydride and the like can also be used instead of acid chloride.

When an aromatic nucleophilic substitution reaction is performed in each step, a nucleophilic agent (e.g., amines, imidazole and the like) and a base (e.g., organic bases and the like) are used as the reagent.

When a nucleophilic addition reaction with carbanion, a nucleophilic 1,4-addition reaction with carbanion (Michael addition reaction) or a nucleophilic substitution reaction with carbanion is performed in each step, examples of the base to be used for developing carbanion include organic lithiums, metal alkoxides, inorganic bases, organic bases and the like.

When the Grignard reaction is performed in each step, examples of the Grignard reagent include aryl magnesium halides such as phenyl magnesium bromide and the like; and alkyl magnesium halides such as methyl magnesium bromide and the like.

The Grignard reagent can be prepared by a method known per se, for example, by reacting alkyl halide or aryl halide with metal magnesium in ether or tetrahydrofuran as a solvent.

When the Knoevenagel condensation reaction is performed in each step, an active methylene compound held between two electron-withdrawing groups (e.g., malonic acid, diethyl malonate, malononitrile and the like) and a base (e.g., organic bases, metal alkoxides, inorganic bases) are used as the reagents.

When the Vilsmeier-Haack reaction is performed in each step, phosphoryl chloride and an amide derivative (e.g., N,N-dimethylformamide and the like) are used as the reagents.

When an azidation reaction of alcohols, alkyl halides or is sulfonate esters is performed in each step, examples of the azidation agent to be used include diphenylphosphoryl azide (DPPA), trimethylsilyl azide, sodium azide and the like. For example, when alcohols are azidated, a method using diphenylphosphoryl azide and 1,8-diazabicyclo[5,4,0]undec-7-ene (DBU), a method using trimethylsilyl azide and the Lewis acid and the like can be employed.

When a reductive amination reaction is performed in each step, examples of the reducing agent to be used include sodium triacetoxyborohydride, sodium cyanoborohydride, hydrogen, formic acid and the like. When the substrate is an amine compound, examples of the carbonyl compound to be used besides para-formaldehyde include aldehydes such as acetaldehyde and the like, ketones such as cyclohexanone and the like. When the substrate is a carbonyl compound, examples of the amines to be used include ammonia; primary amines such as methylamine and the like; secondary amines such as dimethylamine and the like, and the like.

When the Mitsunobu reaction is performed in each step, azodicarboxylate esters (e.g., diethyl azodicarboxylate (DEAD), diisopropyl azodicarboxylate (DIAD) and the like) and triphenylphosphine are used as the reagents.

When an esterification reaction, amidation reaction or ureation reaction is performed in each step, examples of the reagent to be used include halogenated acyl forms such as acid chloride, acid bromide and the like; and activated carboxylic acids such as acid anhydride, active ester form, sulfuric acid ester form and the like. Examples of the carboxylic acid activator include carbodiimide condensing agents such as 1-ethyl-3-(3-dimethylaminopropyl)carbodiimide hydrochloride (WSCD) and the like; triazine condensing agents such as 4-(4,6-dimethoxy-1,3,5-triazin-2-yl)-4-methylmorpholinium chloride-n-hydrate (DMT-MM) and the like; carbonate ester condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methylpyridinium iodide (Mukaiyama reagent); thionyl chloride; $C_{1-6}$ alkyl haloformates such as ethyl chloroformate and the like; O-(7-azabenzotriazol-1-yl)-N,N,N',N'-tetramethyluronium hexafluorophosphate (HATU); sulfuric acid; a combination thereof and the like. When a carbodiimide condensing agent is used, additives such as 1-hydroxybenzotriazole (HOBt), N-hydroxysuccinimide (HOSu), dimethylaminopyridine (DMAP) and the like can be further added to the reaction.

When a coupling reaction is performed in each step, examples of the metal catalyst to be used include palladium compounds such as palladium(II) acetate, tetrakis(triphenylphosphine)palladium(0), dichlorobis(triphenylphosphine) palladium(II), dichlorobis(triethylphosphine)palladium(II), tris(dibenzylideneacetone)dipalladium(0), 1,1'-bis(diphenylphosphino)ferrocene palladium(II) chloride, palladium (II) acetate and the like; nickel compounds such as tetrakis (triphenylphosphine)nickel(0) and the like; rhodium compounds such as tris(triphenylphosphine)rhodium(III)

chloride and the like; a cobalt compound; copper compounds such as copper oxide, copper(I) iodide and the like; a platinum compound and the like. A base may be further added to the reaction and examples of such base include inorganic bases, and the like.

When a thiocarbonylation reaction is performed in each step, diphosphorus pentasulfide is representatively used as a thiocarbonylating agent. Besides diphosphorus pentasulfide, a reagent having a 1,3,2,4-dithiadiphosphetane-2,4-disulfide structure such as 2,4-bis(4-methoxyphenyl-1,3,2,4-dithiadiphosphetane-2,4-disulfide (Lawesson reagent) and the like may also be used.

When the Wohl-Ziegler reaction is performed in each step, examples of the halogenating agent to be used include N-iodosuccinimide, N-bromosuccinimide (NBS), N-chlorosuccinimide (NCS), bromine, sulfuryl chloride and the like. Furthermore, the reaction can be accelerated by adding heat, light, radical initiators such as benzoyl peroxide, azobisisobutyronitrile and the like to the reaction.

When a halogenating reaction of a hydroxy group is performed in each step, examples of the halogenating agent to be used include acid halide of hydrohalic acid and inorganic acid; specifically, hydrochloric acid, thionyl chloride, phosphorus oxychloride and the like for chlorination, and 48% hydrobromic acid and the like for bromination. In addition, a method of obtaining an alkyl halide form from alcohol by reacting with triphenylphosphine and carbon tetrachloride or carbon tetrabromide, and the like may be used. Alternatively, a method of synthesizing an alkyl halide form via a two-step reaction including conversion of alcohol to sulfonic acid ester, and reacting same with lithium bromide, lithium chloride or sodium iodide may also be used.

When the Arbuzov reaction is performed in each step, examples of the reagent to be used include alkyl halides such as ethyl bromoacetate and the like; and phosphites such as triethyl phosphite, tri(isopropyl) phosphite and the like.

When a sulfonic acid esterification reaction is performed in each step, examples of the sulfonylating agent to be used include methanesulfonyl chloride, p-toluenesulfonyl chloride, methanesulfonic anhydride, p-toluenesulfonic anhydride and the like.

When a hydrolysis reaction is performed in each step, an acid or a base is used as the reagent. In addition, when an acid hydrolysis reaction of tert-butyl ester is performed, formic acid, triethylsilane and the like are sometimes added to reductively trap the by-produced tert-butyl cation.

When a dehydration reaction is performed in each step, examples of the dehydrating agent to be used include sulfuric acid, phosphorus pentaoxide, phosphorus oxychloride, N,N'-dicyclohexylcarbodiimide, alumina, polyphosphoric acid and the like.

Compound (I) can be produced by the method shown in the following scheme or a method analogous thereto or the methods described in the Examples.

Compound (I) can be produced from compound (2) or compound (3) by the following method.

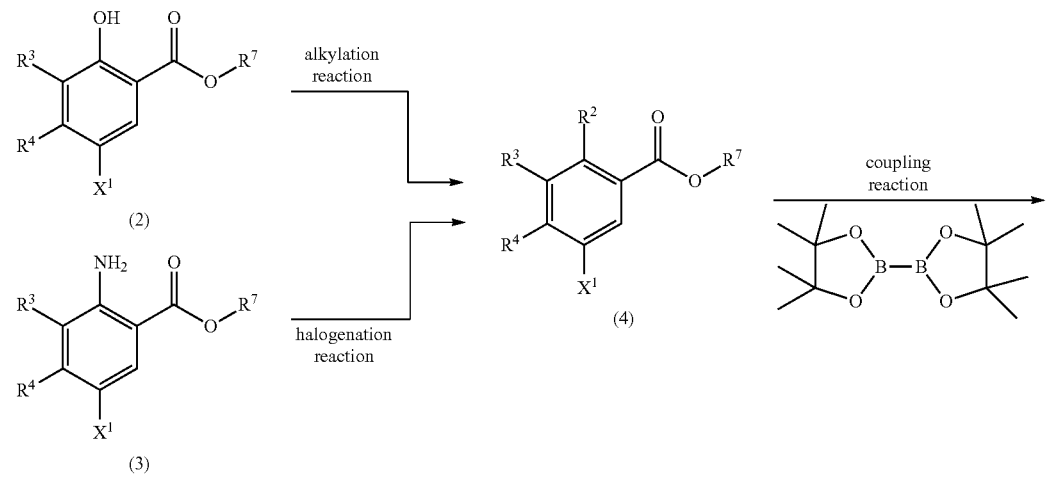

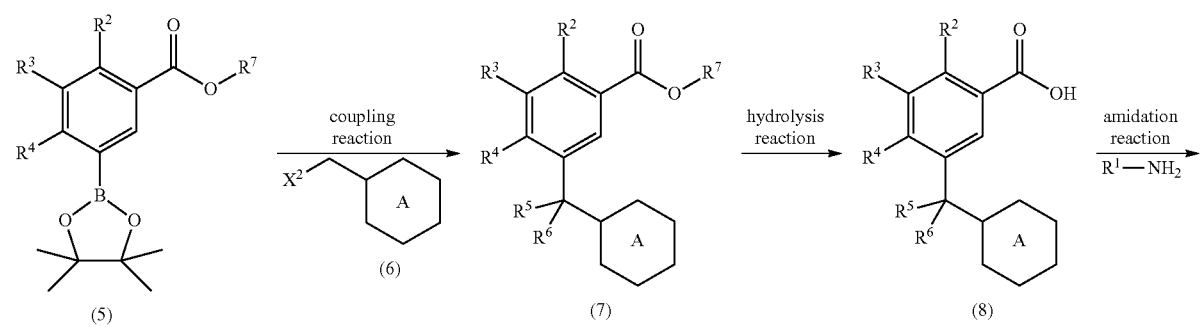

-continued

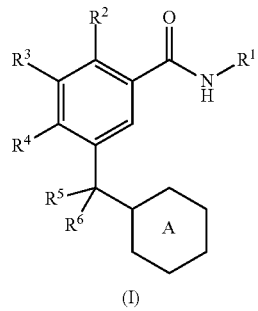

(I)

In the reaction formulas, X1 and $X^2$ are each a halogen atom, $R^7$ is a $C_{1-6}$ alkyl group, and ring A and $R^1$-$R^6$ are as defined above.

Compound (4) can be produced by an alkylation reaction of compound (2). As the alkylating agent to be used, alkyl halides, alkyltriflates, alkyltosylates and the like can be mentioned. A base may be further added to the reaction and, as such base, inorganic bases such as potassium carbonate, sodium hydride and the like can be mentioned.

Compound (4) can also be produced by a halogenation reaction of compound (3). As the halogenating agent to be used, nitrosyl tetrafluoroborate and the like can be mentioned.

Compound (5) can be produced by a coupling reaction of compound (4) and bispinacolate diboron in the presence of a metal catalyst. A base may be added to the reaction and, as such base, inorganic bases such as potassium acetate and the like can be mentioned.

Compound (7) can be produced by a coupling reaction of compound (5) and compound (6) in the presence of a metal catalyst.

Compound (8) can be produced by a hydrolysis reaction of compound (7).

Compound (I) can be produced by an amidation reaction of compound (8) and amines such as $R^1$—$NH_2$ and the like.

Compound (I) can also be produced from compound (9) or compound (4) by the following method.

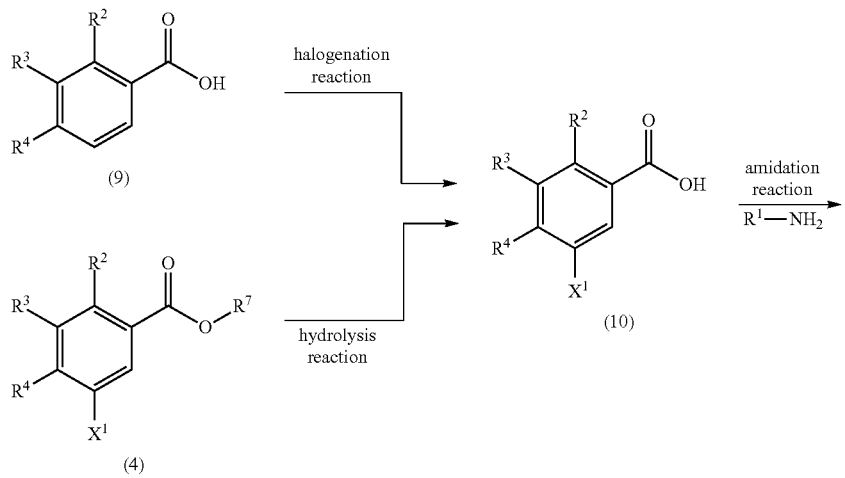

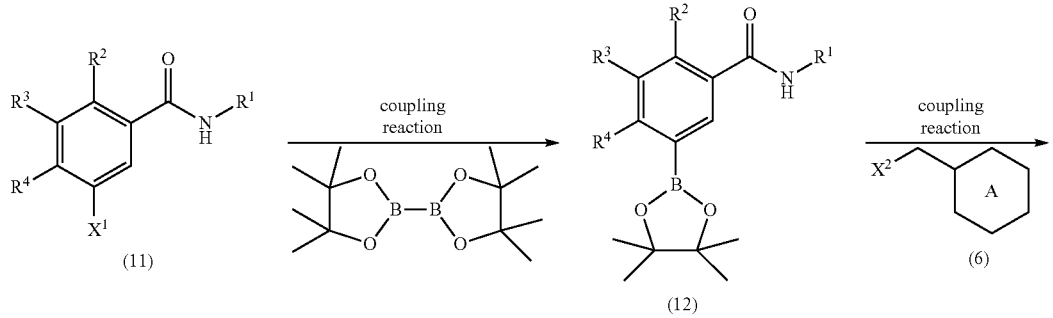

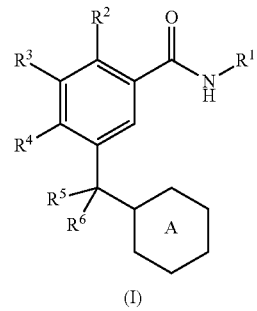

(I)

In the reaction formulas, $X^1$, $X^2$, $R^7$, ring A and $R^1$-$R^6$ are as defined above.

Compound (10) can be produced by a halogenation reaction of compound (9). As the halogenating agent to be used, bromine, hydrobromic acid, N-bromosuccinimide and the like can be mentioned.

Compound (10) can also be produced by a hydrolysis reaction of compound (4).

Compound (11) can be produced by an amidation reaction of compound (10) and amines such as $R^1$—$NH_2$ and the like.

Compound (12) can be produced by a coupling reaction of compound (11) and bispinacolate diboron in the presence of a metal catalyst. A base may be added to the reaction and, as such base, inorganic bases such as potassium acetate and the like can be mentioned.

Compound (I) can be produced by a coupling reaction of compound (12) and compound (6) in the presence of a metal catalyst.

Compound (2), compound (3), compound (6), amines and compound (9) to be used as starting materials when producing Compound (I) can be produced by a method known per se.

Where necessary, in any of the above-mentioned reaction schemes, X1, X2, $R^7$, ring A and $R^1$-$R^6$ in the reaction formulas from compounds (2) to (12) can also be converted by using a general organic reaction singly or using a plurality of general organic reactions in combination, for example, halogenation reaction, acylation reaction, sulfonylation reaction, alkylation reaction, hydrolysis reaction, amination reaction, amidation reaction, esterification reaction, etherification reaction, oxidation reaction, reduction reaction, protection reaction, deprotection reaction, coupling reaction, addition reaction, elimination reaction, substitution reaction and the like.

When compound (I) has an optical isomer, a stereoisomer, a regioisomer or a rotamer, these are also encompassed in compound (I), and can be obtained as a single product according to synthesis and separation methods known per se. For example, when compound (I) contains an optical isomer, an optical isomer resolved from this compound is also encompassed in compound (I).

The optical isomer can be produced according to a method known per se. To be specific, an optically active synthetic intermediate is used, or the final racemate product is subjected to optical resolution according to a conventional method to give an optical isomer.

For example, the method of optical resolution may be a method known per se, such as a fractional recrystallization method, a chiral column method, a diastereomer method etc.

1) Fractional Recrystallization Method

A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine etc.) is formed, which is separated by a fractional recrystallization method, and if desired, a neutralization step to give a free optical isomer.

2) Chiral Column Method

A method wherein a racemate or a salt thereof is applied to a column for separation of an optical isomer (a chiral column) to allow separation. In the case of a liquid chromatography, for example, a mixture of the optical isomers is applied to a chiral column such as ENANTIO-OVM (manufactured by Tosoh Corporation), CHIRAL series (manufactured by Daicel Corporation) and the like, and developed with water, various buffers (e.g., phosphate buffer, etc.) and organic solvents (e.g., ethanol, methanol, isopropanol, acetonitrile, trifluoroacetic acid, diethylamine etc.), solely or as a mixed solution thereof to separate the optical isomer.

3) Diastereomer Method

A method wherein a racemic mixture is prepared into a diastereomeric mixture by chemical reaction with an optically active reagent, which is made into a single substance by a typical separation means (e.g., a fractional recrystallization method, a chromatography method etc.) and the like, and is subjected to a chemical treatment such as hydrolysis reaction and the like to remove an optically active reagent moiety, whereby an optical isomer is obtained. For example, when compound (I) contains hydroxy group, or primary or secondary amino group within a molecule, the compound and an optically active organic acid (e.g., MTPA [α-methoxy-α-(trifluoromethyl)phenylacetic acid], (−)-menthoxyacetic acid etc.) and the like are subjected to condensation reaction to give diastereomers of the ester compound or the amide compound, respectively. When compound (I) has a carboxylic acid group, this compound and an optically active amine or an optically active alcohol reagent are subjected to condensation reaction to give diastereomers of the amide compound or the ester compound, respectively. The separated diastereomer is converted to an optical isomer of the original compound by acid hydrolysis or base hydrolysis reaction.

When compound (I) is obtained as a free compound, the compound can be converted to an objective salt according to a method known per se or a method analogous thereto. Conversely, when it is obtained as a salt, the salt can be converted to a free form or other objective salt by a method known per se or a method analogous thereto.

Compound (I) can be used as a prodrug. The prodrug of compound (I) refers to a compound which is converted to compound (I) as a result of a reaction with an enzyme, gastric acid, etc. under physiological conditions in vivo, thus a compound that undergoes enzymatic oxidation, reduction, hydrolysis etc. to convert to compound (I) and a compound that undergoes hydrolysis and the like by gastric acid, etc. to convert to compound (I).

Examples of the prodrug for compound (I) include a compound obtained by subjecting an amino group in compound (I) to acylation, alkylation or phosphorylation (e.g., a compound obtained by subjecting an amino group in compound (I) to eicosanoylation, alanylation, pentylaminocarbonylation, (5-methyl-2-oxo-1,3-dioxolen-4-yl)methoxycarbonylation, tetrahydrofurylation, pyrrolidylmethylation, pivaloyloxymethylation, tert-butylation and the like); a compound obtained by subjecting a hydroxy group in compound (I) to acylation, alkylation, phosphorylation or boration (e.g., a compound obtained by subjecting a hydroxy group in compound (I) to acetylation, palmitoylation, propanoylation, pivaloylation, succinylation, fumarylation, alanylation or dimethylaminomethylcarbonylation and the like); a compound obtained by subjecting a carboxyl group in compound (I) to esterification or amidation (e.g., a compound obtained by subjecting a carboxyl group in compound (I) to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation and the like) and the like. Any of these compounds can be produced from compound (I) according to a method known per se.

A prodrug of compound (I) may also be one which is converted to compound (I) under physiological conditions as described in "IYAKUHIN no KAIHATSU (Development of Pharmaceuticals)", Vol. 7, Design of Molecules, p. 163-198 (HIROKAWA SHOTEN).

Compound (I) is useful for mammals (e.g., mouse, rat, hamster, rabbit, cat, dog, bovine, sheep, monkey, human etc.) as an agent for the prophylaxis or treatment of diseases, for example, (1) psychiatric diseases [e.g., depression, major depression, bipolar depression, dysthymic disorder, emotional disorder (seasonal affective disorder and the like), recurrent depression, postpartum depression, stress disorder, depression symptom, mania, generalized anxiety disorder, anxiety syndrome, panic disorder, phobia, social phobia, social anxiety disorder, obsessive disorder, post-traumatic stress syndrome, post-traumatic stress disorder, Tourette syndrome, autism, autism spectrum syndrome, fragile X syndrome, Rett syndrome, adjustment disorder, bipolar disorder, neurosis, schizophrenia (e.g., positive symptom, negative symptom, cognitive impairment), cognitive dysfunction associated with schizophrenia, chronic fatigue syndrome, anxiety neurosis, compulsive neurosis, epilepsy, anxiety, anxious mental state, emotional abnormality, cyclothymia, nervous erethism, faint, addiction, low sex drive, attention deficit hyperactivity disorder (ADHD), psychotic major depression, intractable major depression, treatment-resistant depression], (2) neurodegenerative diseases [e.g., Alzheimer's disease, Alzheimer-type senile dementia, Parkinson's disease, Parkinson's disease dementia, Huntington's disease, multi-infarct dementia, frontotemporal dementia, frontotemporal dementia Parkinson's Type, progressive supranuclear palsy, Pick's syndrome, Niemann-Pick syndrome, corticobasal degeneration, Down's syndrome, vascular dementia, post-encephalitic parkinsonism, Lewy body dementia, HIV dementia, amyotrophic lateral sclerosis (ALS), motor neurogenesis disease (MND), Creutzfeldt-Jakob disease or prion disease, cerebral palsy, multiple sclerosis], (3) age-related cognition memory disorders [e.g., age-related memory disorders, senile dementia]

(4) sleep disorders [e.g., intrinsic sleep disorders (e.g., psychophysiological insomnia and the like), extrinsic sleep disorder, circadian rhythm disorders (e.g., time zone change syndrome (jet lag), shift work sleep disorder, irregular sleep-wake pattern, delayed sleep phase syndrome, advanced sleep phase syndrome, non-24-hour sleep-wake and the like), parasomnia, sleep disorders associated with internal medical or psychiatric disorder (e.g., chronic obstructive pulmonary diseases, Alzheimer's disease, Parkinson's disease, cerebrovascular dementia, schizophrenia, depression, anxiety neurosis), stress insomnia, insomnia, insomniac neurosis, sleep apnea syndrome], (5) respiratory depression caused by anesthetics, traumatic disease, or neurodegenerative disease and the like, (6) traumatic brain injury, cerebral apoplexy, neurotic anorexia, eating disorder, anorexia nervosa, hyperorexia, other eating disorder, alcohol dependence, alcohol abuse, alcoholic amnesia, alcohol paranoia, alcohol preference, alcohol withdrawal, alcoholic insanity, alcohol poisoning, alcoholic jealousy, alcoholic mania, alcohol-dependent psychiatric disorder, alcoholic insanity, pharmacophilia, pharmacophobia, pharmacomania, drug withdrawal, migraine, stress headache, catatonic headache, diabetic neuropathy, obesity, diabetes, muscular convulsion, Meniere's disease, autonomic ataxia, alopecia, glaucoma, hypertension, cardiac disease, tachycardia, congestive cardiac failure, breathing, bronchial asthma, apnea, sudden infant death syndrome, inflammatory disease, allergic disease, impotence, climacteric disorder, infertility, cancer, immunodeficiency syndrome caused by HIV infection, immunodeficiency syndrome caused by stress, cerebrospinal meningitis, acromegaly, incontinence, metabolic syndrome, osteoporosis, peptic ulcer, irritable bowel syndrome, inflammatory bowel disease, ulcerative colitis, Crohn's disease, stress gastrointestinal disorder, nervous vomiting, diarrhea, constipation, postoperative ileus, (7) pain.

Compound (I) is particularly preferably useful as a cholinergic muscarinic M1 receptor positive allosteric modulator, for the prophylaxis or treatment of Alzheimer's disease, schizophrenia, pain, sleep disorder, Parkinson's disease dementia, dementia with Lewy bodies and the like.

Since compound (I) has an excellent cholinergic muscarinic M1 receptor positive allosteric modulator activity, it is expected to provide an excellent prophylactic or therapeutic effect for the above-mentioned diseases.

Since compound (I) is superior in solubility in water, the Japanese Pharmacopoeia dissolution test 2nd fluid, or the Japanese Pharmacopoeia disintegration test 2nd fluid, excellent in pharmacokinetics (e.g., plasma drug half-life, brain penetration, metabolic stability, CYP inhibitory), it shows low toxicity (e.g., more excellent as a medicament in terms of acute toxicity, chronic toxicity, genetic toxicity, reproductive toxicity, cardiotoxicity, drug interaction, carcinogenicity, phototoxicity and the like), and also has excellent properties as a pharmaceutical product such as a few side effects and the like, it can be safely administered orally or parenterally to a mammal (e.g., mouse, rat, hamster, rabbit, cat, dog, bovine, sheep, monkey, human and the like). Examples of the "parenteral" include intravenous, intramuscular, subcutaneous, intra-organ, intranasal, intradermal, instillation, intracerebral, intrarectal, intravaginal, intraperitoneal and intratumor administrations, administration to the vicinity of tumor etc. and direct administration to the lesion.

A medicament containing compound (I) (sometimes to be abbreviated as the "medicament of the present invention" in the present specification) may be in any of form (preparation form) of a solid preparation such as powder, granule, tablet, capsule, orally disintegrable film and the like, or a liquid agent such as syrup, emulsion, injection and the like.

The medicament of the present invention can be produced by a conventional method such as blending, kneading, granulation, tableting, coating, sterilization treatment, emulsification and the like according to the form of the preparation. As for the production of the preparation, for example, each item of the Japanese Pharmacopoeia Preparation General Rules and the like can be referred to. In addition, the medicament of the present invention may be formed into a sustained-release preparation containing an active ingredient and a biodegradable polymer compound. The sustained-release preparation can be produced according to the method described in JP-A-9-263545.

In the medicament of the present invention, the content of compound (I) varies depending on the form of the preparation, but is generally 0.01 to 100% by weight, preferably 0.1 to 50% by weight, more preferably 0.5 to 20% by weight, as the amount of compound (I) relative to the whole preparation (whole medicament)

Compound (I) may be used alone or used in admixture with a suitable, pharmacologically acceptable carrier, for example, excipients (e.g., starch, lactose, sucrose, calcium carbonate, calcium phosphate, etc.), binders (e.g., starch, arabic gum, carboxymethyl cellulose, hydroxypropyl cellulose, crystalline cellulose, alginic acid, gelatin, polyvinylpyrrolidone, etc.), lubricants (e.g., stearic acid, magnesium stearate, calcium stearate, talc, etc.), disintegrants (e.g., calcium carboxymethylcellulose, talc, etc.), diluents (e.g., water for injection, physiological saline, etc.) and if desired, with the additives (e.g., a stabilizer, a preservative, a colorant, a fragrance, a solubilizing agent, an emulsifier, a buffer, an isotonic agent, etc.) and the like, by a conventional method, which is processed into a dosage form of a solid agent such as powder, fine granule, granule, tablet, capsule and the like or a liquid agent such as injection and the like, and safely administered orally or parenterally. When compound (I) is formed as a preparation for topical administration, it can also be directly administered to the affected part of an articular disease. In this case, an injection is preferable. The compound can also be administered as a parenteral agent for topical administration (e.g., intramuscular injection, subcutaneous injection, organ injection, injection to the vicinity of a joint and the like, solid preparation such as implant, granule, powder and the like, liquid such as suspension and the like, ointment etc.) and the like.

For formulation into an injection, for example, compound (I) is formulated into an aqueous suspension with a dispersing agent (e.g., surfactant such as Tween 80, HCO-60 and the like, polysaccharides such as carboxymethylcellulose, sodium alginate, hyaluronic acid and the like, polysorbate etc.), preservative (e.g., methylparaben, propylparaben etc.), isotonic agent (e.g., sodium chloride, mannitol, sorbitol, glucose etc.), buffer (e.g., calcium carbonate etc.), pH adjuster (e.g., sodium phosphate, potassium phosphate etc.) and the like to give a practical preparation for injection. In addition, an oily suspension can be obtained by dispersing the compound together with vegetable oil such as sesame oil, corn oil and the like or a mixture thereof with a phospholipid such as lecithin and the like, or medium-chain fatty acid triglyceride (e.g., miglyol 812 etc.) to give an injection to be actually used.

The dose of compound (I) varies depending on the subject of administration, administration route and symptoms and is not particularly limited. For example, for oral administration to adult patients (body weight adult 40 to 80 kg, for example, 60 kg) with Alzheimer's disease, the dose is, for example, 0.001 to 1000 mg/kg body weight/day, preferably 0.01 to 100 mg/kg body weight/day, more preferably 0.1 to 10 mg/kg body weight/day, as compound (I). This amount can be administered in one to three portions per day.

In the medicament of the present invention, compound (I) can be used solely or as a pharmaceutical composition by mixing compound (I) with a pharmacologically acceptable carrier according to a method known per se (e.g., the method described in the Japanese Pharmacopoeia etc.) as the production method of a pharmaceutical preparation. The medicament of the present invention can be safely administered in the form of, for example, a pharmaceutical composition such as tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal administrations, and administration to the lesion).

As the aforementioned "pharmacologically acceptable carrier", various organic or inorganic carriers conventionally used as preparation materials (starting materials) can be used. For example, excipient, lubricant, binder, disintegrant and the like are used for solid preparations, and solvent, solubilizing agent, suspending agent, isotonic agent, buffer, soothing agent and the like are used for liquid preparations. Where necessary, preparation additives such as preservative, antioxidant, colorant, sweetening agent and the like can also be used.

Examples of the excipient include lactose, sucrose, D-mannitol, starch, corn starch, crystalline cellulose, light anhydrous silicic acid and the like.

Examples of the lubricant include magnesium stearate, calcium stearate, talc, colloidal silica and the like.

Examples of the binder include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, sodium carboxymethyl starch, L-hydroxypropylcellulose and the like.

Examples of the solvent include water for injection, alcohol, propylene glycol, macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as poly(vinyl alcohol), polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffer include buffer solutions such as phosphates, acetates, carbonates, citrates and the like.

Examples of the soothing agent include benzyl alcohol and the like.

Examples of the preservative include p-oxybenzoates, chlorobutanol, benzyl alcohol, phenylethyl alcohol, dehydroacetic acid, sorbic acid and the like.

Examples of the antioxidant include sulfite, ascorbic acid, α-tocopherol and the like.

While the pharmaceutical composition varies according to the dosage form, administration method, carrier and the like, it can be produced according to a conventional method by adding compound (I) in a proportion of generally 0.01-100% (w/w), preferably 0.1-95% (w/w), of the total amount of the preparation.

Compound (I) can be used in combination with other active ingredients (hereinafter to be abbreviated as concomitant drug).

Examples of the concomitant drug include the following. benzodiazepine (chlordiazepoxide, diazepam, potassium clorazepate, lorazepam, clonazepam, alprazolam etc.), L-type calcium channel inhibitor (pregabalin etc.), tricyclic or tetracyclic antidepressant (imipramine hydrochloride, amitriptyline hydrochloride, desipramine hydrochloride, clomipramine hydrochloride etc.), selective serotonin reuptake inhibitor (fluvoxamine maleate, fluoxetine hydrochloride, citalopram hydrobromide, sertraline hydrochloride, paroxetine hydrochloride, escitalopram oxalate etc.), serotonin-noradrenaline reuptake inhibitor (venlafaxine hydrochloride, duloxetine hydrochloride, desvenlafaxine hydrochloride etc.), noradrenaline reuptake inhibitor (reboxetine mesylate etc.), noradrenaline-dopamine reuptake inhibitor (bupropion hydrochloride etc.), mirtazapine, trazodone hydrochloride, nefazodone hydrochloride, bupropion hydrochloride, setiptiline maleate, 5-HT1A agonist (buspirone hydrochloride, tandospirone citrate, osemozotan hydrochloride etc.), 5-$HT_3$ antagonist (cyamemazine etc.), non-cardioselective β inhibitor (propranolol hydrochloride, oxprenolol hydrochloride etc.), histamine $H_1$ antagonist (hydroxyzine hydrochloride etc.), therapeutic drug for schizophrenia (chlorpromazine, haloperidol, sulpiride, clozapine, trifluoperazine hydrochloride, fluphenazine hydrochloride, olanzapine, quetiapine fumarate, risperidone, aripiprazole etc.), CRF antagonist, other antianxiety drug (meprobamate etc.), tachykinin antagonist (aprepitant, saredutant etc.), medicament that acts on metabotropic glutamate receptor, CCK antagonist, β adrenaline antagonist (amibegron hydrochloride etc.), GAT-1 inhibitor (tiagabine hydrochloride etc.), N-type calcium channel inhibitor, carbonic anhydrase II inhibitor, NMDA glycine site agonist, NMDA antagonist (memantine etc.), peripheral benzodiazepine receptor agonist, vasopressin antagonist, vasopressin V1b antagonist, vasopressin V1a antagonist, phosphodiesterase inhibitor, opioid antagonist, opioid agonist, uridine, nicotinic acid receptor agonist, thyroid hormone (T3, T4), TSH, TRH, MAO inhibitor (phenelzine sulfate, tranylcypromine sulfate, moclobemide etc.), 5-$HT_{2A}$ antagonist, 5-$HT_{2A}$ inverse agonist, COMT inhibitor (entacapone etc.), therapeutic drug for bipolar disorder (lithium carbonate, sodium valproate, lamotrigine, riluzole, felbamate etc.), cannabinoid CB1 antagonist (rimonabant etc.), FAAH inhibitor, sodium channel inhibitor, anti-ADHD drug (methylphenidate hydrochloride, methamphetamine hydrochloride etc.), therapeutic drug for alcoholism, therapeutic drug for autism, therapeutic drug for chronic fatigue syndrome, therapeutic drug for convulsion, therapeutic drug for fibromyalgia syndrome, therapeutic drug for headache, therapeutic drug for insomnia (etizolam, zopiclone, triazolam, zolpidem, ramelteon, indiplon etc.), therapeutic drug for quitting smoking, therapeutic drug for myasthenia gravis, therapeutic drug for cerebral infarction, therapeutic drug for mania, therapeutic drug for hypersomnia, therapeutic drug for pain, therapeutic drug for dysthymia, therapeutic drug for autonomic ataxia, therapeutic drug for male and female sexual dysfunction, therapeutic drug for migraine, therapeutic drug for pathological gambler, therapeutic drug for restless legs syndrome, therapeutic drug for substance addiction, therapeutic drug for alcohol-related syndrome, therapeutic drug for irritable bowel syndrome, therapeutic drug for Alzheimer's disease (donepezil, galanthamine, memantine, rivastigmine etc.), therapeutic drug for Parkinson's disease (levodopa, carbidopa, benserazide, selegiline, rasagiline, zonisamide, entacapone, amantadine, talipexole, pramipexole, ropinirole, rotigotine, apomorphine, Cabergoline, Pergolide, bromocriptine, istradefylline, trihexyphenidyl, biperiden, pyrroheptyne, profenamine, promethazine, droxidopa, combination of these medicaments etc.), Parkinson's disease dementia (rivastigmine), therapeutic drug for dementia with Lewy bodies (donepezil), therapeutic drug for ALS (riluzole, neurotrophic factor etc.), therapeutic drug for lipid abnormality such as cholesterol-lowering drug (statin series (pravastatin sodium, atorvastatin, simvastatin, rosuvastatin etc.), fibrate (clofibrate etc.), squalene synthetase inhibitor), therapeutic drug for behavior abnormalities or suppressant of dromomania due to dementia (sedatives, antianxiety drug etc.), apoptosis inhibitor, antiobesity drug, therapeutic drug for diabetes, therapeutic drug for hypertension, therapeutic drug for hypotension, therapeutic drug for rheumatism (DMARD), anti-cancer agent, therapeutic drug for hypothyroidism (PTH), calcium receptor antagonist, sex hormone or a derivative thereof (progesterone, estradiol, estradiol benzoate etc.), neuronal differentiation promoter, nerve regeneration promoter, non-steroidal anti-inflammatory drug (meloxicam, tenoxicam, indomethacin, ibuprofen, celecoxib, rofecoxib, aspirin etc.), steroid (dexamethasone, cortisone acetate etc.), anti-cytokine drug (TNF inhibitor, MAP kinase inhibitor etc.), antibody medicament, nucleic acid or nucleic acid derivative, aptamer drug and the like.

By combining compound (I) and a concomitant drug, a superior effect such as (1) the dose can be reduced as compared to single administration of compound (I) or a concomitant drug, (2) the drug to be combined with compound (I) can be selected according to the condition of patients (mild case, severe case and the like), (3) the period of treatment can be set longer by selecting a concomitant drug having different action and mechanism from compound (I), (4) a sustained treatment effect can be designed by selecting a concomitant drug having different action and mechanism from compound (I), (5) a synergistic effect can be afforded by a combined use of compound (I) and a concomitant drug, and the like, can be achieved.

Hereinafter compound (I) and a concomitant drug used in combination are referred to as the "combination agent of the present invention".

When using the combination agent of the present invention, the administration time of compound (I) and the concomitant drug is not restricted, and compound (I) or a pharmaceutical composition thereof and the concomitant drug or a pharmaceutical composition thereof can be administered to an administration subject simultaneously, or may be administered at different times. The dosage of the concomitant drug may be determined according to the dose clinically used, and can be appropriately selected depending on an administration subject, administration route, disease, combination and the like.

The administration mode of the combination agent of the present invention is not particularly restricted, and it is sufficient that compound (I) and the concomitant drug are combined in administration. Examples of such administration mode include the following methods:
(1) administration of a single preparation obtained by simultaneously processing compound (I) and the concomitant drug,
(2) simultaneous administration of two kinds of preparations of compound (I) and the concomitant drug, which have been separately produced, by the same administration route, (3) administration of two kinds of preparations of compound (I) and the concomitant drug, which have been separately produced, by the same administration route in a staggered manner, (4) simultaneous administration of two kinds of preparations of compound (I) and the concomitant drug, which have been separately produced, by different administration routes, (5) administration of two kinds of preparations of compound (I) and the concomitant drug, which have been separately produced, by different administration routes in a staggered manner (e.g., administration in the order of compound (I) and the concomitant drug, or in the reverse order) and the like.

The combination agent of the present invention exhibits low toxicity. For example, compound (I) or (and) the aforementioned concomitant drug can be combined with a pharmacologically acceptable carrier according to the known method to prepare a pharmaceutical composition such as tablets (including sugar-coated tablet and film-coated tablet), powders, granules, capsules (including soft capsule), liquids, injections, suppositories, sustained-release agents, etc. These compositions can be administered safely orally or non-orally (e.g., topical, rectal, intravenous administration etc.). Injection can be administered intravenously, intramuscularly, subcutaneously, or by intraorgan administration or directly to the lesion.

Examples of the pharmacologically acceptable carriers usable for the production of a combination agent of the present invention, various organic or inorganic carrier substances conventionally used as preparation materials can be mentioned. For solid preparations, for example, excipient, lubricant, binder and disintegrant can be used. For liquid preparations, for example, solvent, solubilizing agent, suspending agent, isotonic agent, buffering agent, soothing agent and the like can be used. Where necessary, an appropriate amount of additives such as conventional preservative, antioxidant, colorant, sweetening agent, adsorbent, wetting agent and the like can be used as appropriate.

Examples of the excipient include lactose, sucrose, D-mannitol, starch, corn starch, crystalline cellulose, light anhydrous silicic acid and the like.

Examples of the lubricant include magnesium stearate, calcium stearate, talc, colloidal silica and the like.

Examples of the binder include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, sodium carboxymethyl starch, L-hydroxypropylcellulose and the like.

Examples of the solvent include water for injection, alcohol, propylene glycol, macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as poly(vinyl alcohol), polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffer include buffer solutions such as phosphates, acetates, carbonates, citrates and the like.

Examples of the soothing agent include benzyl alcohol and the like.

Examples of the preservative include p-oxybenzoates, chlorobutanol, benzyl alcohol, phenylethyl alcohol, dehydroacetic acid, sorbic acid and the like.

Examples of the antioxidant include sulfite, ascorbic acid, α-tocopherol and the like.

The mixing ratio of compound (I) to the concomitant drug in the combination agent of the present invention can be appropriately selected depending on an administration subject, administration route, diseases and the like.

For example, the content of compound (I) in the combination agent of the present invention differs depending on the form of a preparation, and usually from about 0.01 to about 100 wt %, preferably from about 0.1 to about 50 wt %, further preferably from about 0.5 to about 20 wt %, based on the whole preparation.

The content of the concomitant drug in the combination agent of the present invention differs depending on the form of a preparation, and usually from about 0.01 to about 100 wt %, preferably from about 0.1 to about 50 wt %, further preferably from about 0.5 to about 20 wt %, based on the whole preparation.

The content of additives such as a carrier and the like in the combination agent of the present invention differs depending on the form of a preparation, and usually from about 1 to about 99.99 wt %, preferably from about 10 to about 90 wt %, based on the whole preparation.

When compound (I) and a concomitant drug are separately formulated into preparations, the contents thereof are similar to the above.

EXAMPLES

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

In silica gel column chromatography, NH means use of aminopropylsilane-bound silica gel. In HPLC (high performance liquid chromatography), C18 means use of octadecyl-bound silica gel. The ratios of elution solvents are volume mixing ratios, unless otherwise specified.

In the following Examples, the following abbreviations are used.
MS: mass spectrum
M: mol concentration
N: normality
$CDCl_3$: deuterochloroform
DMSO: dimethyl sulfoxide
DMSO-$d_6$: deuterodimethyl sulfoxide
$^1$H NMR: proton nuclear magnetic resonance spectrum
LC/MS: liquid chromatograph mass spectrometer
ESI: Electron Spray Ionization
APCI: atmospheric pressure chemical ionization
DME: 1,2-dimethoxyethane
DMF: N,N-dimethylformamide
HATU: 2-(7-azabenzotriazol-1-yl)-1,1,3,3-tetramethyluronium hexafluorophosphate
WSC: 1-ethyl-3-(3-dimethylaminopropyl)carbodiimide $^1$H NMR was measured by Fourier-transform NMR. For the analysis, ACD/SpecManager (trade name) and the like were used. Very mild peaks for protons of a hydroxy group, an amino group and the like are not described.

MS was measured by LC/MS. As Ionization, ESI method or APCI method was used. The data indicates those found. Generally, a molecular ion peak ([M+H]$^+$, [M−H]$^−$ and the like) is observed. In the case of a compound having a tert-butoxycarbonyl group, a peak after elimination of a tert-butoxycarbonyl group or tert-butyl group is observed as a fragment ion. In the case of a compound having a hydroxyl group, a peak after elimination of $H_2O$ may be observed as a fragment ion. In the case of a salt, a molecular ion peak or fragment ion peak of free form is generally observed.

The unit of reagent concentration (c) in optical rotation ([α]$_D$) is g/100 mL.

As the elemental analytical values (Anal.), calculated values (Calcd) and measured values (Found) are described.

Example 5

N-(trans-2-hydroxycyclohexyl)-2-methoxy-3,4-dimethyl-5-(4-(1-methyl-1H-1,2,3-triazol-4-yl)benzyl)benzamide A) methyl 5-bromo-2-methoxy-3,4-dimethylbenzoate A mixture of methyl 5-bromo-2-hydroxy-3,4-dimethylbenzoate (500 mg), iodomethane (0.181 mL), potassium carbonate (800 mg) and DMF (10 mL) was stirred at 70° C. for 5 hr. The reaction mixture was poured into water, and the mixture was extracted with ethyl acetate. The organic layer was washed with brine, dried over magnesium sulfate, and concentrated under reduced pressure. The residue was purified by silica gel column chromatography (ethyl acetate/hexane) to give the title compound (473 mg).
MS: [M+H]$^+$ 273.1, 275.0

B) methyl 2-methoxy-3,4-dimethyl-5-(4,4,5,5-tetramethyl-1,3,2-dioxaborolan-2-yl)benzoate To a mixture of methyl 5-bromo-2-methoxy-3,4-dimethylbenzoate (472 mg), 4,4,4',4',5,5,5',5'-octamethyl-2,2'-bi-1,3,2-dioxaborolane (658 mg), potassium acetate (509 mg) and toluene (10 mL) was added dichlorobis(triphenylphosphine)palladium(II) (60.6 mg) under an argon atmosphere. The mixture was stirred under an argon atmosphere at 110° C. for 8 hr. The reaction mixture was diluted with ethyl acetate and filtered. The filtrate was washed with water, dried over magnesium sulfate, filtered, and concentrated under reduced pressure. The residue was purified by silica gel column chromatography (ethyl acetate/hexane) to give the title compound (477 mg).
MS: [M+H]$^+$ 321.2

C) methyl 2-methoxy-3,4-dimethyl-5-(4-(1-methyl-1H-1,2,3-triazol-4-yl)benzyl)benzoate A mixture of methyl 2-methoxy-3,4-dimethyl-5-(4,4,5,5-tetramethyl-1,3,2-dioxaborolan-2-yl)benzoate (0.106 g), 4-(4-(bromomethyl)phenyl)-1-methyl-1H-1,2,3-triazole (0.125 g), tetrakis(triphenylphosphine)palladium(0) (0.019 g), 2 M aqueous sodium carbonate solution (0.331 mL) and DME (3.31 mL) was heated under a nitrogen atmosphere at 90° C. for 15 hr. After cooling, the reaction mixture was diluted with water and extracted with ethyl acetate. The extract was washed with saturated brine, dried over magnesium sulfate, and concentrated under reduced pressure. The residue was purified by silica gel column chromatography (ethyl acetate/hexane) to give the title compound (0.090 g).
MS: [M+H]$^+$ 366.2

D) 2-methoxy-3,4-dimethyl-5-(4-(1-methyl-1H-1,2,3-triazol-4-yl)benzyl)benzoic acid A mixture of methyl 2-methoxy-3,4-dimethyl-5-(4-(1-methyl-1H-1,2,3-triazol-4-yl)benzyl)benzoate (0.09 g), 8 M aqueous sodium hydroxide solution (1.5 mL), tetrahydrofuran (1.5 mL), water (1.5 mL), and ethanol (1.5 mL) was stirred at 50° C. for 2 hr. The reaction mixture was neutralized with 1 M hydrochloric acid and extracted with ethyl acetate. The organic layer was washed with saturated brine, dried over magnesium sulfate, and concentrated under reduced pressure to give the title compound (83 mg).
MS: [M+H]$^+$ 352.2

E) N-(trans-2-hydroxycyclohexyl)-2-methoxy-3,4-dimethyl-5-(4-(1-methyl-1H-1,2,3-triazol-4-yl)benzyl)benzamide A mixture of 2-methoxy-3,4-dimethyl-5-(4-(1-methyl-1H-1,2,3-triazol-4-yl)benzyl)benzoic acid (49 mg), trans-2-aminocyclohexanol hydrochloride (21.1 mg), triethylamine (0.049 mL), WSC hydrochloride (32.1 mg), 1-hydroxybenzotriazole (22.6 mg) and DMF (1 mL) was stirred at room temperature overnight. To the reaction mixture were added WSC hydrochloride (32.1 mg) and 1-hydroxybenzotriazole (22.6 mg). The reaction mixture was stirred at 50° C. for 3 hr. To the reaction mixture was added 5% aqueous sodium hydrogen carbonate solution at room temperature, and the mixture was extracted with ethyl acetate. The organic layer was washed with brine, dried over sodium sulfate, and concentrated under reduced pressure. The residue was purified by silica gel column chromatography (ethyl acetate/ methanol) and recrystallized from ethyl acetate/hexane to give the title compound (49.1 mg).

$^1$H NMR (300 MHz, CDCl$_3$) δ 1.22-1.50 (4H, m), 1.77 (2H, d, J=11.0 Hz), 2.07 (2H, brs), 2.15 (3H, s), 2.23 (3H, s), 3.47 (1H, d, J=9.9 Hz), 3.76 (3H, s), 3.88 (2H, d, J=4.1 Hz), 4.04 (2H, s), 4.13 (3H, s), 7.16 (2H, d, J=8.3 Hz), 7.64-7.75 (3H, m), 7.82 (1H, s), 8.03 (1H, d, J=6.7 Hz).

Example 10

N-(trans-2-hydroxycyclohexyl)-2-methoxy-3,4-dimethyl-5-(4-(1-methyl-1H-1,2,3-triazol-4-yl)benzyl) benzamide (optical isomer, short retention time)

N-(trans-2-hydroxycyclohexyl)-2-methoxy-3,4-dimethyl-5-(4-(1-methyl-1H-1,2,3-triazol-4-yl)benzyl)benzamide (38.8 mg) was optically resolved by HPLC (CHIRALPAK AD, 50 mmI.D.×500 mmL, mobile phase:hexane/2-propanol) to give the title compound (17.9 mg) having a short retention time.

$^1$H NMR (300 MHz, CDCl$_3$) δ 1.30-1.49 (4H, m), 1.76 (2H, d, J=8.8 Hz), 2.05-2.14 (2H, m), 2.15 (3H, s), 2.23 (3H, s), 3.39-3.51 (1H, m), 3.76 (3H, s), 3.79-3.96 (2H, m), 4.04 (2H, s), 4.13 (3H, s), 7.15 (2H, d, J=8.2 Hz), 7.62-7.75 (3H, m), 7.81 (1H, s), 8.02 (1H, d, J=6.9 Hz).

Example 12

2-fluoro-N-((3S,4S)-4-hydroxytetrahydro-2H-pyran-3-yl)-3,4-dimethyl-5-(4-(1H-pyrazol-1-yl)benzyl) benzamide alias: (1,5-anhydro-2,4-dideoxy-2-((2-fluoro-3,4-dimethyl-5-(4-(1H-pyrazol-1-yl)benzyl) benzoyl)amino)-L-threo-pentitol)

A) methyl 5-bromo-2-fluoro-3,4-dimethylbenzoate

To a mixture of methyl 2-amino-5-bromo-3,4-dimethylbenzoate (1.01 g) and (trifluoromethyl)benzene (10 mL) was gradually added nitrosyl tetrafluoroborate (750 mg) at 0° C. The mixture was stirred at 0° C. for 1 hr and at 100° C. for 2 hr. To the reaction mixture was added ice water at 0° C., and the mixture was extracted with ethyl acetate. The organic layer was dried over magnesium sulfate and concentrated under reduced pressure. The residue was purified by silica gel column chromatography (ethyl acetate/hexane) to give the title compound (0.938 g).

$^1$H NMR (300 MHz, DMSO-d$_6$) δ 2.26 (3H, d, J=2.6 Hz), 2.40 (3H, s), 3.84 (3H, s), 7.88 (1H, d, J=6.8 Hz).

B) methyl 2-fluoro-3,4-dimethyl-5-(4,4,5,5-tetramethyl-1,3,2-dioxaborolan-2-yl)benzoate A mixture of methyl 5-bromo-2-fluoro-3,4-dimethylbenzoate (0.47 g), bis(pinacolato)diboron (0.69 g), dichlorobis (triphenylphosphine)palladium(II) (0.063 g), potassium acetate (0.35 g) and toluene (18 mL) was stirred under a nitrogen atmosphere at 90° C. for 15 hr. After cooling, the reaction mixture was diluted with water and extracted with ethyl acetate. The organic layer was washed with saturated brine, dried over magnesium sulfate, and concentrated under reduced pressure. The residue was purified by silica gel column chromatography (ethyl acetate/hexane) to give the title compound (510 mg).
MS: [M+H]$^+$ 309.2

C) methyl 5-(4-(1H-pyrazol-1-yl)benzyl)-2-fluoro-3, 4-dimethylbenzoate

A mixture of methyl 2-fluoro-3,4-dimethyl-5-(4,4,5,5-tetramethyl-1,3,2-dioxaborolan-2-yl)benzoate (0.51 g), 1-(4-(chloromethyl)phenyl)-1H-pyrazole (0.48 g), tetrakis (triphenylphosphine)palladium(0) (0.096 g), 2 M aqueous sodium carbonate solution (1.7 mL), and DME (17 mL) was stirred under a nitrogen atmosphere at 90° C. for 15 hr. After cooling, the reaction mixture was diluted with water and extracted with ethyl acetate. The extract was washed with saturated brine, dried over magnesium sulfate, and concentrated under reduced pressure. The residue was purified by silica gel column chromatography (ethyl acetate/hexane) to give the title compound (0.35 g).
MS: [M+H]$^+$ 339.1

D) 5-(4-(1H-pyrazol-1-yl)benzyl)-2-fluoro-3,4-dimethylbenzoic acid

A mixture of methyl 5-(4-(1H-pyrazol-1-yl)benzyl)-2-fluoro-3,4-dimethylbenzoate (0.35 g), 8 N aqueous sodium hydroxide solution (5 mL), tetrahydrofuran (5 mL), water (5 mL), and ethanol (5 mL) was stirred at 50° C. for 2 hr. The reaction mixture was neutralized with 1 M hydrochloric acid and extracted with ethyl acetate. The organic layer was washed with saturated brine, dried over magnesium sulfate, and concentrated under reduced pressure to give the title compound (330 mg).
MS: [M+H]$^+$ 325.1

E) 2-fluoro-N-((3S,4S)-4-hydroxytetrahydro-2H-pyran-3-yl)-3,4-dimethyl-5-(4-(1H-pyrazol-1-yl) benzyl)benzamide alias: (1,5-anhydro-2,4-dideoxy-2-((2-fluoro-3,4-dimethyl-5-(4-(1H-pyrazol-1-yl) benzyl)benzoyl)amino)-L-threo-pentitol)

To a mixture of 5-(4-(1H-pyrazol-1-yl)benzyl)-2-fluoro-3,4-dimethylbenzoic acid (56 mg) and (3S,4S)-3-aminotetrahydro-2H-pyran-4-ol (24 mg) in DMF (1.5 mL) were added WSC hydrochloride (50 mg) and 1-hydroxybenzotriazole (38 mg) at room temperature, and the mixture was stirred at room temperature for 4 hr. To the reaction mixture was added aqueous sodium hydrogen carbonate solution, and the mixture was extracted 3 times with ethyl acetate. The organic layer was dried over magnesium sulfate and concentrated under reduced pressure. The residue was purified by silica gel column chromatography (hexane/ethyl acetate) and concentrated, and the precipitate was collected by filtration and washed with isopropyl ether/ethyl acetate to give the title compound (64 mg).

$^1$H NMR (300 MHz, DMSO-d$_6$) δ 1.37-1.58 (1H, m), 1.89 (1H, d, J=12.1 Hz), 2.10-2.23 (6H, m), 3.08 (1H, dd, J=10.9, 8.7 Hz), 3.27-3.38 (1H, m), 3.54-3.75 (2H, m), 3.76-3.91 (2H, m), 4.04 (2H, s), 4.93 (1H, d, J=5.3 Hz), 6.45-6.58 (1H, m), 7.23 (2H, d, J=8.3 Hz), 7.35 (1H, d, J=7.5 Hz), 7.66-7.80 (3H, m), 7.91 (1H, dd, J=7.0, 3.6 Hz), 8.43 (1H, d, J=2.3 Hz).

Example 13

N-((3S,4S)-4-hydroxytetrahydro-2H-pyran-3-yl)-2-methoxy-3,4-dimethyl-5-(4-(1-methyl-1H-1,2,3-triazol-4-yl)benzyl)benzamide alias: 1,5-anhydro-2, 4-dideoxy-2-((2-methoxy-3,4-dimethyl-5-(4-(1-methyl-1H-1,2,3-triazol-4-yl)benzyl)benzoyl) amino)-L-threo-pentitol To a mixture of 2-methoxy-3,4-dimethyl-5-(4-(1-methyl-1H-1,2,3-triazol-4-yl)benzyl)benzoic acid (201 mg), 2-amino-1,5-anhydro-2,4-dideoxy-L-threo-pentitol (74 mg), 1-hydroxybenzotriazole (108 mg) and DMF (5 mL) was added WSC hydrochloride (154 mg), and the mixture was stirred at room temperature for 16 hr. To the reaction mixture was added aqueous sodium hydrogen carbonate solution, and the mixture was extracted with ethyl acetate. The organic layer was washed with brine, dried over magnesium sulfate, and concentrated under reduced pressure. The residue was purified by silica gel column chromatography (ethyl acetate/methanol) and freeze-dried to give the title compound (222 mg).

$^1$H NMR (300 MHz, DMSO-$d_6$) δ 1.50 (1H, td, J=8.8, 4.3 Hz), 1.80-1.97 (1H, m), 2.17 (6H, d, J=11.3 Hz), 3.15 (1H, dd, J=10.9, 8.0 Hz), 3.25-3.46 (1H, m), 3.53-4.16 (12H, m), 5.00 (1H, d, J=5.1 Hz), 7.18 (2H, d, J=8.3 Hz), 7.43 (1H, s), 7.73 (2H, d, J=8.3 Hz), 8.14 (1H, d, J=7.4 Hz), 8.44 (1H, s).

Example 14

N-((1S,2S)-2-hydroxycyclohexyl)-2-methoxy-3,4-dimethyl-5-(4-(1H-1,2,3-triazol-1-yl)benzyl)benzamide A) 1-(4-(chloromethyl)phenyl)-1H-1,2,3-triazole To thionyl chloride (8.25 mL) was gradually added (4-(1H-1,2,3-triazol-1-yl)phenyl)methanol (0.99 g). The mixture was stirred at room temperature for 15 hr. The reaction mixture was concentrated under reduced pressure and diluted with ethyl acetate and saturated aqueous sodium hydrogen carbonate solution. The organic layer was washed with saturated aqueous sodium hydrogen carbonate solution, water and saturated brine, dried over magnesium sulfate, and concentrated under reduced pressure to give the title compound (1.04 g).

MS: [M+H]$^+$ 194.1

B) methyl 2-methoxy-3,4-dimethyl-5-(4-(1H-1,2,3-triazol-1-yl)benzyl)benzoate

A mixture of methyl 2-methoxy-3,4-dimethyl-5-(4,4,5,5-tetramethyl-1,3,2-dioxaborolan-2-yl)benzoate (150 mg), 1-(4-(chloromethyl)phenyl)-1H-1,2,3-triazole (136 mg), tetrakis(triphenylphosphine)palladium(0) (27 mg), 2 M aqueous sodium carbonate solution (0.468 mL), and DME (4.68 mL) was stirred under a nitrogen atmosphere at 90° C. for 15 hr. After cooling, the reaction mixture was diluted with water and extracted with ethyl acetate. The extract was washed with saturated brine, dried over magnesium sulfate, and concentrated under reduced pressure. The residue was purified by silica gel column chromatography (ethyl acetate/hexane) to give the title compound (155 mg).

MS: [M+H]$^+$ 352.2

C) 2-methoxy-3,4-dimethyl-5-(4-(1H-1,2,3-triazol-1-yl)benzyl)benzoic acid

A mixture of methyl 2-methoxy-3,4-dimethyl-5-(4-(1H-1,2,3-triazol-1-yl)benzyl)benzoate (150 mg), 8 M aqueous sodium hydroxide solution (2 mL), tetrahydrofuran (2 mL), water (2 mL), and ethanol (2 mL) was stirred at 50° C. for 2 hr. The reaction mixture was neutralized with 1N hydrochloric acid and extracted with ethyl acetate. The organic layer was washed with brine, dried over sodium sulfate, and concentrated under reduced pressure to give the title compound (120 mg).

MS: [M+H]$^+$ 338.1

D) N-((1S,2S)-2-hydroxycyclohexyl)-2-methoxy-3,4-dimethyl-5-(4-(1H-1,2,3-triazol-1-yl)benzyl)benzamide To a mixture of 2-methoxy-3,4-dimethyl-5-(4-(1H-1,2,3-triazol-1-yl)benzyl)benzoic acid (120 mg), (1S,2S)-2-aminocyclohexanol (45 mg), 1-hydroxybenzotriazole 1 hydrate (65 mg), triethylamine (0.074 mL), and DMF (2.37 mL) was added WSC hydrochloride (82 mg). The reaction mixture was stirred at room temperature for 15 hr. The reaction mixture was diluted with water and extracted with ethyl acetate. The extract was washed with water and saturated brine, dried over magnesium sulfate, and concentrated under reduced pressure. The residue was purified by silica gel column chromatography (ethyl acetate/hexane) and recrystallized from ethyl acetate/hexane to give the title compound (120 mg).

$^1$H NMR (300 MHz, DMSO-$d_6$) δ 1.11-1.33 (4H, m), 1.53-1.69 (2H, m), 1.82-2.05 (2H, m), 2.15 (3H, s), 2.19 (3H, s), 3.26-3.42 (1H, m), 3.52-3.66 (1H, m), 3.69 (3H, s), 4.08 (2H, s), 4.67 (1H, d, J=5.5 Hz), 7.28-7.37 (2H, m), 7.42 (1H, s), 7.75-7.85 (2H, m), 7.95 (1H, d, J=1.1 Hz), 8.03 (1H, d, J=7.5 Hz), 8.76 (1H, d, J=1.1 Hz).

Example 24

1,5-anhydro-2,3-dideoxy-3-((2-methoxy-3,4-dimethyl-5-(4-(1-methyl-1H-1,2,3-triazol-4-yl)benzyl)benzoyl)amino)-L-threo-pentitol To a mixture of 2-methoxy-3,4-dimethyl-5-(4-(1-methyl-1H-1,2,3-triazol-4-yl)benzyl)benzoic acid (0.083 g), 3-amino-1,5-anhydro-2,3-dideoxy-L-threo-pentitol hydrochloride (0.040 g), 1-hydroxybenzotriazole 1 hydrate (0.043 g), triethylamine (0.082 mL) and DMF (1.575 mL) was added WSC hydrochloride (0.054 g). The mixture was stirred at room temperature for 15 hr. The reaction mixture was diluted with water and extracted with ethyl acetate. The extract was washed with water and saturated brine, dried over magnesium sulfate, and concentrated under reduced pressure. The residue was purified by silica gel column chromatography (ethyl acetate/hexane) and recrystallized from ethyl acetate/hexane to give the title compound (70 mg).

$^1$H NMR (300 MHz, DMSO-$d_6$) δ 1.40-1.62 (1H, m), 1.90-2.01 (1H, m), 2.14 (3H, s), 2.18 (3H, s), 3.00-3.11 (1H, m), 3.27-3.53 (2H, m), 3.69 (3H, s), 3.73-3.87 (3H, m), 4.01 (2H, s), 4.07 (3H, s), 4.98 (1H, d, J=5.7 Hz), 7.15-7.22 (2H, m), 7.38 (1H, s), 7.69-7.77 (2H, m), 8.12 (1H, d, J=7.4 Hz), 8.44 (1H, s).

Example 25

1,5-anhydro-2,4-dideoxy-2-((2,3-difluoro-4-methyl-5-(4-(1H-pyrazol-1-yl)benzyl)benzoyl)amino)-L-threo-pentitol A) 5-bromo-2,3-difluoro-4-methylbenzoic acid To a mixture of 2,3-difluoro-4-methylbenzoic acid (800 mg), acetic acid (15 mL), water (3 mL), and nitric acid (3.9 mL) was added bromine (0.476 mL) at room temperature. To the mixture was gradually added a solution of silver nitrate (1.58 g) in water (3 mL), and the mixture was stirred at room temperature for 3 hr. The precipitate was filtered off and washed with acetic acid. The filtrate was concentrated under reduced pressure. The residue was dissolved in ethyl acetate, washed with 1 M hydrochloric acid and brine, dried over sodium sulfate, and concentrated under reduced pressure. The residue was washed with hexane to give the title compound (455 mg).

$^1$H NMR (300 MHz, DMSO-$d_6$) δ 2.36 (3H, d, J=2.6 Hz), 7.84 (1H, dd, J=6.2, 2.1 Hz), 13.75 (1H, br s).

B) 1,5-anhydro-2-((5-bromo-2,3-difluoro-4-methylbenzoyl)amino)-2,4-dideoxy-L-threo-pentitol To a mixture of 5-bromo-2,3-difluoro-4-methylbenzoic acid (1 g), 2-amino-1,5-anhydro-2,4-dideoxy-L-threo-pentitol (0.513 g) and tetrahydrofuran (39.8 mL) was added 4-(4,6-dimethoxy-1,3,5-triazin-2-yl)-4-methylmorpholin-4-ium chloride hydrate (1.528 g) at room temperature. The mixture was stirred at room temperature for 3 days. The reaction mixture was diluted with water and saturated brine at room temperature and extracted with ethyl acetate. The extract was dried over magnesium sulfate, filtered, concentrated under reduced pressure and powderized with ethyl acetate/hexane to give the title compound (1.366 g).

MS: [M+H]$^+$ 350.0

C) 1,5-anhydro-2,4-dideoxy-2-((2,3-difluoro-4-methyl-5-(4,4,5,5-tetramethyl-1,3,2-dioxaborolan-2-yl)benzoyl)amino)-L-threo-pentitol To a mixture of 1,5-anhydro-2-((5-bromo-2,3-difluoro-4-methylbenzoyl)amino)-2,4-dideoxy-L-threo-pentitol (0.1 g) and toluene (1.43 mL) were added 4,4,4',4',5,5,5',5'-octamethyl-2,2'-bi-1,3,2-dioxaborolane (0.080 g), potassium acetate (0.084 g), and dichlorobis(triphenylphosphine)palladium(II) (0.020 g) at room temperature. The mixture was heated under reflux under a nitrogen atmosphere for 5 hr. The reaction mixture was diluted with water and saturated brine and extracted with ethyl acetate. The extract was dried over magnesium sulfate, filtered, concentrated under reduced pressure and purified by silica gel column chromatography (ethyl acetate/hexane) to give the title compound (0.049 g).

MS: [M+H]$^+$ 398.2

D) 1,5-anhydro-2,4-dideoxy-2-((2,3-difluoro-4-methyl-5-(4-(1H-pyrazol-1-yl)benzyl)benzoyl)amino)-L-threo-pentitol To a mixture of 1,5-anhydro-2,4-dideoxy-2-((2,3-difluoro-4-methyl-5-(4,4,5,5-tetramethyl-1,3,2-dioxaborolan-2-yl)benzoyl)amino)-L-threo-pentitol (0.0487 g) and DME (1.103 mL)/water (0.123 mL) were added 1-(4-(chloromethyl)phenyl)-1H-pyrazole (0.028 g), sodium carbonate (0.026 g), and tetrakis(triphenylphosphine)palladium(0) (0.014 g) at room temperature. The mixture was heated under a nitrogen atmosphere at 80° C. for 16 hr. The reaction mixture was diluted with water and saturated brine and extracted with ethyl acetate. The extract was dried over magnesium sulfate, filtered, concentrated under reduced pressure and purified by silica gel column chromatography (ethyl acetate/hexane). The purified product was recrystallized from ethyl acetate/hexane to give the title compound (0.022 g).

$^1$H NMR (300 MHz, DMSO-$d_6$) δ 1.46 (1H, d, J=10.5 Hz), 1.89 (1H, d, J=9.4 Hz), 2.18 (3H, d, J=2.3 Hz), 3.03-3.14 (1H, m), 3.27-3.38 (1H, m), 3.53-3.88 (4H, m), 4.06 (2H, s), 4.97 (1H, d, J=5.3 Hz), 6.52 (1H, t, J=2.3 Hz), 7.22-7.33 (3H, m), 7.69-7.80 (3H, m), 8.18 (1H, d, J=7.5 Hz), 8.45 (1H, d, J=2.6 Hz).

Example 26

1,5-anhydro-2,4-dideoxy-2-((2-methoxy-3,4-dimethyl-5-(4-(1-methyl-1H-pyrazol-3-yl)benzyl)benzoyl)amino)-L-threo-pentitol

A) 5-bromo-2-methoxy-3,4-dimethylbenzoic acid

To a mixture of methyl 5-bromo-2-methoxy-3,4-dimethylbenzoate (5 g) and methanol (50 mL) was added 2N aqueous sodium hydroxide solution (18.4 mL). The mixture was stirred at room temperature overnight. The reaction mixture was concentrated, diluted with water and washed with ethyl acetate. The aqueous layer was acidified with 2 M hydrochloric acid and extracted with ethyl acetate. The organic layer was dried over anhydrous sodium sulfate, filtered, and concentrated to give the title compound (4.5 g).

MS: [M+H]$^+$ 259.0

B) 1,5-anhydro-2-((5-bromo-2-methoxy-3,4-dimethylbenzoyl)amino)-2,4-dideoxy-L-threo-pentitol To a mixture of 5-bromo-2-methoxy-3,4-dimethylbenzoic acid (4.4 g) and dichloromethane (100 mL) were added HATU (7.77 g), triethylamine (7.1 mL) and 2-amino-1,5-anhydro-2,4-dideoxy-L-threo-pentitol (1.99 g). The mixture was stirred at room temperature overnight. The reaction mixture was washed twice with water. The organic layer was dried over anhydrous sodium sulfate, filtered, and concentrated. The residue was purified by silica gel column chromatography (petroleum ether/ethyl acetate) to give the title compound (6.0 g).

MS: [M+H]$^+$ 358.0

C) 1,5-anhydro-2,4-dideoxy-2-((2-methoxy-3,4-dimethyl-5-(4,4,5,5-tetramethyl-1,3,2-dioxaborolan-2-yl)benzoyl)amino)-L-threo-pentitol A mixture of 1,5-anhydro-2-((5-bromo-2-methoxy-3,4-dimethylbenzoyl)amino)-2,4-dideoxy-L-threo-pentitol (6 g), 4,4,4',4',5,5,5',5'-octamethyl-2,2'-bi-1,3,2-dioxaborolane (8.53 g), potassium acetate (4.94 g), dichlorobis(triphenylphosphine)palladium(II) (1.18 g) and toluene (100 mL) was stirred at 100° C. overnight. The insoluble material was filtered off and the filtrate was concentrated under reduced pressure. The residue was purified by silica gel column chromatography (petroleum ether/ethyl acetate) to give the title compound (6.5 g).

MS: [M+H]$^+$ 406.1

D) 1,5-anhydro-2,4-dideoxy-2-((2-methoxy-3,4-dimethyl-5-(4-(1-methyl-1H-pyrazol-3-yl)benzyl)benzoyl)amino)-L-threo-pentitol A mixture of 1,5-anhydro-2,4-dideoxy-2-((2-methoxy-3,4-dimethyl-5-(4,4,5,5-tetramethyl-1,3,2-dioxaborolan-2-yl)benzoyl)amino)-L-threo-pentitol (200 mg), 3-(4-(bromomethyl)phenyl)-1-methyl-1H-pyrazole (135 mg), sodium carbonate (104 mg), [1,1'-bis(diphenylphosphino)ferrocene]palladium(II) dichloride dichloromethane adduct (8 mg) and DME (4 mL)/water (1 mL) was stirred under microwave radiation at 100° C. for 1 hr. The reaction mixture was cooled to room temperature, diluted with water and extracted 3 times with ethyl acetate. The combined organic layer was dried over anhydrous sodium sulfate, filtered, and concentrated. The residue was purified by preparative HPLC (C18, water/acetonitrile, containing ammonium bicarbonate) to give the title compound (90 mg).

$^1$H NMR (400 MHz, CDCl$_3$) δ 1.74-1.78 (1H, m), 2.07-2.12 (1H, m), 2.15 (3H, s), 2.24 (3H, s), 3.34-3.39 (1H, m), 3.48-3.57 (2H, m), 3.77 (3H, s), 3.82-3.86 (1H, m), 3.95-4.02 (4H, m), 4.05-4.08 (3H, m), 4.14-4.18 (1H, m), 6.49 (1H, d, J=2.0 Hz), 7.13 (2H, d, J=8.0 Hz), 7.36 (1H, d, J=2.4 Hz), 7.68 (2H, d, J=8.0 Hz), 7.84 (1H, s), 8.23 (1H, d, J=7.2 Hz).

Example 28

1,5-anhydro-2,4-dideoxy-2-((5-((6-(1,3-dimethyl-1H-pyrazol-4-yl)pyridin-3-yl)methyl)-2-methoxy-3,4-dimethylbenzoyl)amino)-L-threo-pentitol A) 6-(1,3-dimethyl-1H-pyrazol-4-yl)nicotinaldehyde To a mixture of 6-chloronicotinaldehyde (7 g) and dioxane (400 mL)/water (10 mL) were added [1,1'-bis(diphenylphosphino)ferrocene]palladium(II) dichloride (500 mg), potassium carbonate (13.8 g), and 1,3-dimethyl-4-(4,4,5,5-tetramethyl-1,3,2-dioxaborolan-2-yl)-1H-pyrazole (16.5 g). The mixture was stirred under a nitrogen atmosphere at 110° C. for 16 hr. The reaction mixture was concentrated. The residue was purified by silica gel column chromatography (petroleum ether/ethyl acetate) to give the title compound (8.0 g).

MS: [M+H]$^+$ 202.1

B) (6-(1,3-dimethyl-1H-pyrazol-4-yl)pyridin-3-yl)methanol

To a mixture of 6-(1,3-dimethyl-1H-pyrazol-4-yl)nicotinaldehyde (8.0 g) and methanol (300 mL) was added sodium borohydride (4.5 g) at 00° C. The mixture was stirred at room temperature for 16 hr. To the reaction mixture was added water at 0° C. The aqueous layer was extracted 3 times with dichloromethane. The combined organic layer was washed with water and brine, dried over sodium sulfate and concentrated under reduced pressure to give the title compound (6.0 g).

MS: [M+H]$^+$ 204.1

C) 5-(chloromethyl)-2-(1,3-dimethyl-1H-pyrazol-4-yl)pyridine

To a mixture of (6-(1,3-dimethyl-1H-pyrazol-4-yl)pyridin-3-yl)methanol (6.0 g) and dichloromethane (150 mL) was added thionyl chloride (10.5 g) at 0° C. The mixture was stirred at room temperature for 16 hr. To the reaction mixture was added water, and the mixture was adjusted to pH 7 with aqueous sodium hydrogen carbonate solution. The aqueous layer was extracted with dichloromethane. The organic layer was washed with brine, dried over sodium sulfate, and concentrated under reduced pressure. The residue was purified by silica gel column chromatography (petroleum ether/ethyl acetate) to give the title compound (4.5 g).

MS: [M+H]$^+$ 222.1

D) 1,5-anhydro-2,4-dideoxy-2-((5-((6-(1,3-dimethyl-1H-pyrazol-4-yl)pyridin-3-yl)methyl)-2-methoxy-3,4-dimethylbenzoyl)amino)-L-threo-pentitol A mixture of 1,5-anhydro-2,4-dideoxy-2-((2-methoxy-3,4-dimethyl-5-(4,4,5,5-tetramethyl-1,3,2-dioxaborolan-2-yl)benzoyl)amino)-L-threo-pentitol (200 mg), 5-(chloromethyl)-2-(1,3-dimethyl-1H-pyrazol-4-yl)pyridine (119 mg), sodium carbonate (104 mg), [1,1'-bis(diphenylphosphino)ferrocene]palladium(II) dichloride dichloromethane adduct (8 mg) and DME (4 mL)/water (1 mL) was stirred under microwave radiation at 100° C. for 1 hr. The reaction mixture was cooled to room temperature, diluted with water and extracted 3 times with ethyl acetate. The combined organic layers were dried over anhydrous sodium sulfate, filtered, and concentrated. The residue was purified by preparative HPLC (C18, water/acetonitrile, containing ammonium bicarbonate) to give the title compound (175 mg).

$^1$H NMR (400 MHz, CDCl$_3$) δ 1.71-1.77 (1H, m), 2.06-2.12 (1H, m), 2.18 (3H, s), 2.25 (3H, s), 2.50 (3H, s), 3.35-3.39 (1H, m), 3.47-3.49 (1H, m), 3.51-3.57 (1H, m), 3.77 (3H, s), 3.81-3.86 (1H, m), 3.88 (3H, s), 3.96-4.02 (3H, m), 4.04-4.10 (1H, m), 4.14-4.18 (1H, m), 7.31 (1H, d, J=8.0 Hz), 7.37 (1H, dd, J=8.0, 2.0 Hz), 7.77 (1H, s), 7.83 (1H, s), 8.24 (1H, d, J=7.2 Hz), 8.38 (1H, d, J=1.2 Hz).

Example 29

1,5-anhydro-2,4-dideoxy-2-((5-(4-(1,3-dimethyl-1H-pyrazol-4-yl)benzyl)-2-methoxy-3,4-dimethylbenzoyl)amino)-L-threo-pentitol A) 4-(4-(bromomethyl)phenyl)-1,3-dimethyl-1H-pyrazole To a mixture of (4-(1,3-dimethyl-1H-pyrazol-4-yl)phenyl)methanol (2.70 g) and dichloromethane (50 mL) was added dropwise phosphorus tribromide (10.8 g) at 0° C. The mixture was stirred at 18° C. for 16 hr. The reaction mixture was poured into saturated aqueous sodium hydrogen carbonate solution at 0° C., the organic layer was separated, and the aqueous layer was extracted two times with dichloromethane. The combined organic layer was dried over sodium sulfate, and concentrated under reduced pressure. The residue was purified by silica gel column chromatography (petroleum ether/ethyl acetate) to give the title compound (2.70 g).

MS: [M+H]$^+$ 264.9

B) 1,5-anhydro-2,4-dideoxy-2-((5-(4-(1,3-dimethyl-1H-pyrazol-4-yl)benzyl)-2-methoxy-3,4-dimethylbenzoyl)amino)-L-threo-pentitol A mixture of 1,5-anhydro-2,4-dideoxy-2-((2-methoxy-3,4-dimethyl-5-(4,4,5,5-tetramethyl-1,3,2-dioxaborolan-2-yl)benzoyl)amino)-L-threo-pentitol (200 mg), 4-(4-(bromomethyl)phenyl)-1,3-dimethyl-1H-pyrazole (143 mg), sodium carbonate (104 mg), [1,1'-bis(diphenylphosphino)ferrocene]palladium(II) dichloride dichloromethane adduct (8 mg) and DME (4 mL)/water (1 mL) was stirred under microwave radiation at 100° C. for 1 hr. The reaction mixture was cooled to room temperature, diluted with water and extracted 3 times with ethyl acetate. The combined organic layer was dried over anhydrous sodium sulfate, filtered, and concentrated. The residue was purified by silica gel column chromatography (dichloromethane/methanol) to give the title compound (120 mg).

$^1$H NMR (400 MHz, CDCl$_3$) δ 1.71-1.79 (1H, m), 2.07-2.13 (1H, m), 2.20 (3H, s), 2.26 (3H, s), 2.38 (3H, s), 3.34-3.41 (2H, m), 3.51-3.57 (1H, m), 3.78 (3H, s), 3.80-3.84 (1H, m), 3.88 (3H, s), 3.97-4.10 (4H, m), 4.14-4.18

(1H, m), 7.12 (2H, d, J=8.0 Hz), 7.27 (1H, s), 7.29 (1H, s), 7.40 (1H, s), 7.84 (1H, s), 8.23 (1H, d, J=7.2 Hz).

Example 32

1,5-anhydro-2,4-dideoxy-2-((2-fluoro-3,4-dimethyl-5-(4-(1,3-thiazol-4-yl)benzyl)benzoyl)amino)-L-threo-pentitol A) 5-bromo-2-fluoro-3,4-dimethylbenzoic acid To a mixture of methyl 5-bromo-2-fluoro-3,4-dimethylbenzoate (4 g) and methanol (25 mL) was added 8 M aqueous sodium hydroxide solution (9.58 mL) at room temperature. The mixture was stirred at room temperature for 1 hr. The reaction mixture was concentrated under reduced pressure, acidified with 6 M hydrochloric acid at 0° C. and poured into water. The precipitate was collected by filtration, washed with water and dried under reduced pressure to give the title compound (3.67 g).
MS: [M+H]$^+$ 247.0, 249.0

B) 1,5-anhydro-2-((5-bromo-2-fluoro-3,4-dimethylbenzoyl)amino)-2,4-dideoxy-L-threo-pentitol A mixture of 2-amino-1,5-anhydro-2,4-dideoxy-L-threo-pentitol (2.088 g), 5-bromo-2-fluoro-3,4-dimethylbenzoic acid (3.67 g), WSC hydrochloride (4.27 g), 1-hydroxybenzotriazole (3.01 g) and DMF (70 mL) was stirred under an argon atmosphere at room temperature for 16 hr. To the reaction mixture was added water at room temperature, and the mixture was extracted with ethyl acetate. The organic layer was washed with water and brine, dried over magnesium sulfate, and concentrated under reduced pressure. The residue was purified by silica gel column chromatography (ethyl acetate/hexane) to give the title compound (4.94 g).
MS: [M+H]$^+$ 346.1, 348.1

C) 1,5-anhydro-2,4-dideoxy-2-((2-fluoro-3,4-dimethyl-5-(4,4,5,5-tetramethyl-1,3,2-dioxaborolan-2-yl)benzoyl)amino)-L-threo-pentitol To a mixture of 1,5-anhydro-2-((5-bromo-2-fluoro-3,4-dimethylbenzoyl)amino)-2,4-dideoxy-L-threo-pentitol (4.94 g), 4,4,4',4',5,5,5',5'-octamethyl-2,2'-bi-1,3,2-dioxaborolane (4.71 g), potassium acetate (4.20 g) and toluene (100 mL) was added dichlorobis(triphenylphosphine)palladium(II) (0.501 g) under an argon atmosphere. The mixture was stirred under an argon atmosphere at 110° C. for 6 hr. To the reaction mixture was added 5% aqueous sodium hydrogen carbonate solution, and the mixture was extracted with ethyl acetate. The organic layer was washed with brine, dried over sodium sulfate, and concentrated under reduced pressure. The residue was purified by silica gel column chromatography (ethyl acetate/hexane) and crystallized from ethyl acetate/hexane to give the title compound (3.82 g).
MS: [M+H]$^+$ 394.2

D) 1,5-anhydro-2,4-dideoxy-2-((2-fluoro-3,4-dimethyl-5-(4-(1,3-thiazol-4-yl)benzyl)benzoyl)amino)-L-threo-pentitol To a mixture of 1,5-anhydro-2,4-dideoxy-2-((2-fluoro-3,4-dimethyl-5-(4,4,5,5-tetramethyl-1,3,2-dioxaborolan-2-yl)benzoyl)amino)-L-threo-pentitol (150 mg), sodium carbonate (121 mg), 4-(4-(bromomethyl)phenyl)-1,3-thiazole (116 mg) and DME (10 mL)/water (3 mL) was added tetrakis(triphenylphosphine)palladium(0) (22.04 mg) at room temperature. The mixture was stirred under an argon atmosphere at 80° C. overnight. To the reaction mixture was added water at room temperature, and the mixture was extracted with ethyl acetate. The organic layer was washed with water and brine, dried over magnesium sulfate, and concentrated under reduced pressure. The residue was purified by silica gel column chromatography (ethyl acetate/hexane) and crystallized from ethyl acetate/hexane to give the title compound (130 mg).
$^1$H NMR (300 MHz, DMSO-d$_6$) δ 1.37-1.55 (1H, m), 1.89 (1H, dd, J=12.8, 3.2 Hz), 2.11-2.23 (6H, m), 3.09 (1H, dd, J=10.9, 8.8 Hz), 3.25-3.41 (1H, m), 3.52-3.89 (4H, m), 4.04 (2H, s), 4.93 (1H, d, J=5.1 Hz), 7.19 (2H, d, J=8.1 Hz), 7.35 (1H, d, J=7.4 Hz), 7.90 (3H, d, J=8.3 Hz), 8.09 (1H, d, J=1.9 Hz), 9.17 (1H, d, J=1.9 Hz).

The compounds of Examples 1-4, 6-9, 11, 12, 15-23, 27, 30-31 and 33-47 in Table 1 were produced according to is the above-mentioned production method, the methods shown in the Examples, or a method analogous thereto. The Example compounds are shown in Table 1. In the Table, MS shows measured values.

TABLE 1

| Ex. No. | IUPAC name | structural formula | MS |
|---|---|---|---|
| 1 | N-(trans-2-hydroxycyclopentyl)-2-methoxy-4-methyl-5-(4-(1H-pyrazol-1-yl)benzyl)benzamide | | 406.2 |

TABLE 1-continued

| Ex. No. | IUPAC name | structural formula | MS |
|---|---|---|---|
| 2 | N-(trans-2-hydroxycyclopentyl)-2-methoxy-3,4-dimethyl-5-(4-(1H-pyrazol-1-yl)benzyl)benzamide | | 420.1 |
| 3 | 3-fluoro-N-(trans-2-hydroxycyclopentyl)-4-methyl-5-(4-(1H-pyrazol-1-yl)benzyl)benzamide | | 394.2 |
| 4 | N-(trans-2-hydroxycyclopentyl)-2-methoxy-3,4-dimethyl-5-(4-(1-methyl-1H-1,2,3-triazol-4-yl)benzyl)benzamide | | 435.2 |
| 5 | N-(trans-2-hydroxycyclohexyl)-2-methoxy-3,4-dimethyl-5-(4-(1-methyl-1H-1,2,3-triazol-4-yl)benzyl)benzamide | | 449.1 |

TABLE 1-continued

| Ex. No. | IUPAC name | MS |
|---|---|---|
| 6 | 2-methoxy-3,4-dimethyl-5-(4-(1-methyl-1H-1,2,3-triazol-4-yl)benzyl)-N-(tetrahydrofuran-2-ylmethyl)benzamide | 435.2 |
| 7 | 3-fluoro-N-(trans-2-hydroxycyclohexyl)-2-methoxy-4-methyl-5-(4-(1H-pyrazol-1-yl)benzyl)benzamide | 438.1 |
| 8 | 3-fluoro-N-(trans-2-hydroxycyclopentyl)-2-methoxy-4-methyl-5-(4-(1H-pyrazol-1-yl)benzyl)benzamide | 424.2 |

TABLE 1-continued

| Ex. No. | IUPAC name | structural formula | MS |
|---|---|---|---|
| 9 | 3-fluoro-2-methoxy-4-methyl-5-(4-(1H-pyrazol-1-yl)benzyl)-N-(tetrahydrofuran-2-ylmethyl)benzamide | | 424.1 |
| 10 | N-(trans-2-hydroxycyclohexyl)-2-methoxy-3,4-dimethyl-5-(4-(1-methyl-1H-1,2,3-triazol-4-yl)benzyl)benzamide (optical isomer, shorter retention time) | | 449.1 |
| 11 | N-(trans-2-hydroxycyclohexyl)-2-methoxy-3,4-dimethyl-5-(4-(1-methyl-1H-1,2,3-triazol-4-yl)benzyl)benzamide (optical isomer, longer retention time) | | 449.1 |

TABLE 1-continued

| Ex. No. | IUPAC name | structural formula | MS |
|---|---|---|---|
| 12 | 2-fluoro-N-((3S,4S)-4-hydroxytetrahydro-2H-pyran-3-yl)-3,4-dimethyl-5-(4-(1H-pyrazol-1-yl)benzyl)benzamide<br>another name: (1,5-anhydro-2,4-dideoxy-2-((2-fluoro-3,4-dimethyl-5-(4-(1H-pyrazol-1-yl)benzyl)benzoyl)amino)-L-threo-pentitol) | | 424.1 |
| 13 | N-((3S,4S)-4-hydroxytetrahydro-2H-pyran-3-yl)-2-methoxy-3,4-dimethyl-5-(4-(1-methyl-1H-1,2,3-triazol-4-yl)benzyl)benzamide<br>another name: 1,5-anhydro-2,4-dideoxy-2-((2-methoxy-3,4-dimethyl-5-(4-(1-methyl-1H-1,2,3-triazol-4-yl)benzyl)benzoyl)amino)-L-threo-pentitol | | 451.2 |
| 14 | N-((1S,2S)-2-hydroxycyclohexyl)-2-methoxy-3,4-dimethyl-5-(4-(1H-1,2,3-triazol-1-yl)benzyl)benzamide | | 435.2 |

TABLE 1-continued

| Ex. No. | IUPAC name | structural formula | MS |
|---|---|---|---|
| 15 | 2-ethoxy-N-((1S,2S)-2-hydroxycyclohexyl)-3,4-dimethyl-5-(4-(1-methyl-1H-1,2,3-triazol-4-yl)benzyl)benzamide | | 463.2 |
| 16 | N-((1S,2S)-2-hydroxycyclohexyl)-2-isopropoxy-3,4-dimethyl-5-(4-(1-methyl-1H-1,2,3-triazol-4-yl)benzyl)benzamide | | 477.3 |
| 17 | 2-(cyclopropylmethoxy)-N-((1S,2S)-2-hydroxycyclohexyl)-3,4-dimethyl-5-(4-(1-methyl-1H-1,2,3-triazol-4-yl)benzyl)benzamide | | 489.3 |

TABLE 1-continued

| Ex. No. | IUPAC name | structural formula | MS |
|---|---|---|---|
| 18 | 2-(difluoromethoxy)-N-((1S,2S)-2-hydroxycyclohexyl)-3,4-dimethyl-5-(4-(1-methyl-1H-1,2,3-triazol-4-yl)benzyl)benzamide | | 485.2 |
| 19 | 2-fluoro-N-((1S,2S)-2-hydroxycyclopentyl)-3,4-dimethyl-5-((6-(1H-pyrazol-1-yl)pyridin-3-yl)methyl)benzamide | | 409.2 |
| 20 | 2-fluoro-N-((1S,2S)-2-hydroxycyclohexyl)-3,4-dimethyl-5-((6-(1H-pyrazol-1-yl)pyridin-3-yl)methyl)benzamide | | 423.2 |

TABLE 1-continued

| Ex. No. | IUPAC name | structural formula | MS |
|---|---|---|---|
| 21 | N-((1S,2S)-2-hydroxycyclohexyl)-2-methoxy-3,4-dimethyl-5-((6-(1-methyl-1H-pyrazol-3-yl)pyridin-3-yl)methyl)benzamide | | 449.2 |
| 22 | N-((1S,2S)-2-hydroxycyclopentyl)-2-methoxy-3,4-dimethyl-5-((6-(1-methyl-1H-pyrazol-3-yl)pyridin-3-yl)methyl)benzamide | | 435.2 |
| 23 | N-((1S,2S)-2-hydroxycyclohexyl)-2-methoxy-3,4-dimethyl-5-((6-methylpyridin-3-yl)methyl)benzamide | | 383.0 |
| 24 | 1,5-anhydro-2,3-dideoxy-3-((2-methoxy-3,4-dimethyl-5-(4-(1-methyl-1H-1,2,3-triazol-4-yl)benzyl)benzoyl)amino)-L-threo-pentitol | | 451.2 |

TABLE 1-continued

| Ex. No. | IUPAC name | structural formula | MS |
|---|---|---|---|
| 25 | 1,5-anhydro-2,4-dideoxy-2-((2,3-difluoro-4-methyl-5-(4-(1H-pyrazol-1-yl)benzyl)benzoyl)amino)-L-threo-pentitol | | 428.2 |
| 26 | 1,5-anhydro-2,4-dideoxy-2-((2-methoxy-3,4-dimethyl-5-(4-(1-methyl-1H-pyrazol-3-yl)benzyl)benzoyl)amino)-L-threo-pentitol | | 450.1 |
| 27 | 1,5-anhydro-2,4-dideoxy-2-((2-methoxy-3,4-dimethyl-5-(4-(1H-pyrazol-1-yl)benzyl)benzoyl)amino)-L-threo-pentitol | | 436.2 |

TABLE 1-continued

| Ex. No. | IUPAC name | structural formula | MS |
|---|---|---|---|
| 28 | 1,5-anhydro-2,4-dideoxy-2-((5-((6-(1,3-dimethyl-1H-pyrazol-4-yl)pyridin-3-yl)methyl)-2-methoxy-3,4-dimethylbenzoyl)amino)-L-threo-pentitol | | 465.2 |
| 29 | 1,5-anhydro-2,4-dideoxy-2-((5-(4-(1,3-dimethyl-1H-pyrazol-4-yl)benzyl)-2-methoxy-3,4-dimethylbenzoyl)amino)-L-threo-pentitol | | 464.3 |
| 30 | 1,5-anhydro-2,4-dideoxy-2-((2-methoxy-3,4-dimethyl-5-((6-(1H-pyrazol-1-yl)pyridin-3-yl)methyl)benzoyl)amino)-L-threo-pentitol | | 437.2 |

TABLE 1-continued

| Ex. No. | IUPAC name | structural formula | MS |
|---|---|---|---|
| 31 | 1,5-anhydro-2,4-dideoxy-2-((2-methoxy-3,4-dimethyl-5-((6-(1-methyl-1H-pyrazol-3-yl)pyridin-3-yl)methyl)benzoyl)amino)-L-threo-pentitol | | 451.2 |
| 32 | 1,5-anhydro-2,4-dideoxy-2-((2-fluoro-3,4-dimethyl-5-(4-(1,3-thiazol-4-yl)benzyl)benzoyl)amino)-L-threo-pentitol | | 441.1 |
| 33 | 1,5-anhydro-2,4-dideoxy-2-((2-fluoro-3,4-dimethyl-5-(4-(2-methyl-1,3-oxazol-4-yl)benzyl)benzoyl)amino)-L-threo-pentitol | | 439.2 |

TABLE 1-continued

| Ex. No. | IUPAC name | structural formula | MS |
|---|---|---|---|
| 34 | 1,5-anhydro-2,4-dideoxy-2-((2-methoxy-3,4-dimethyl-5-(4-(1,3-thiazol-4-yl)benzyl)benzoyl)amino)-L-threo-pentitol | | 453.2 |
| 35 | 1,5-anhydro-2,3-dideoxy-3-((2-fluoro-3,4-dimethyl-5-(4-(1H-pyrazol-1-yl)benzyl)benzoyl)amino)-L-threo-pentitol | | 424.2 |
| 36 | 1,5-anhydro-2,4-dideoxy-2-((2-methoxy-3,4-dimethyl-5-(4-(2-methyl-1,3-oxazol-4-yl)benzyl)benzoyl)amino)-L-threo-pentitol | | 451.2 |

TABLE 1-continued

| Ex. No. | IUPAC name | structural formula | MS |
|---|---|---|---|
| 37 | 2-fluoro-N-((3S,4R)-4-hydroxytetrahydrofuran-3-yl)-3,4-dimethyl-5-(4-(1H-pyrazol-1-yl)benzyl)benzamide | | 410.2 |
| 38 | 1,5-anhydro-2,4-dideoxy-2-((2-fluoro-3,4-dimethyl-5-(4-(1-methyl-1H-pyrazol-3-yl)benzyl)benzoyl)amino)-L-threo-pentitol | | 438.2 |
| 39 | 1,5-anhydro-2,4-dideoxy-2-((5-((6-(1,3-dimethyl-1H-pyrazol-4-yl)pyridin-3-yl)methyl)-2-fluoro-3,4-dimethylbenzoyl)amino)-L-threo-pentitol | | 453.3 |

TABLE 1-continued
| Ex. No. | IUPAC name | structural formula | MS |
|---|---|---|---|
| 40 | 1,5-anhydro-2,4-dideoxy-2-((2-fluoro-3,4-dimethyl-5-((6-(1H-pyrazol-1-yl)pyridin-3-yl)methyl)benzoyl)amino)-L-threo-pentitol | 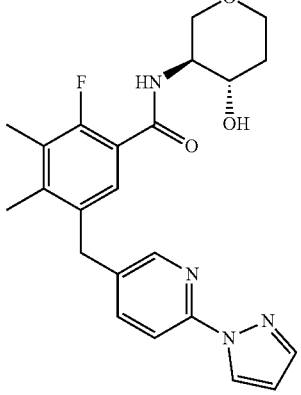 | 425.2 |
| 41 | 1,5-anhydro-2,4-dideoxy-2-((2-fluoro-3,4-dimethyl-5-((6-(1-methyl-1H-pyrazol-3-yl)pyridin-3-yl)methyl)benzoyl)amino)-L-threo-pentitol | 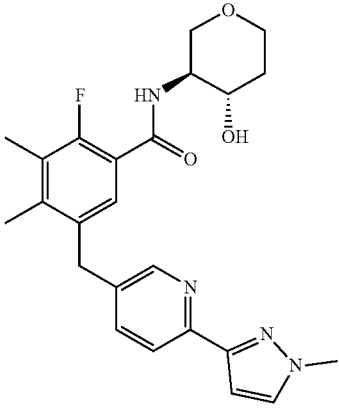 | 439.3 |
| 42 | 1,5-anhydro-2,4-dideoxy-2-((2-fluoro-3,4-dimethyl-5-(4-(1-methyl-1H-1,2,3-triazol-4-yl)benzyl)benzoyl)amino)-L-threo-pentitol | 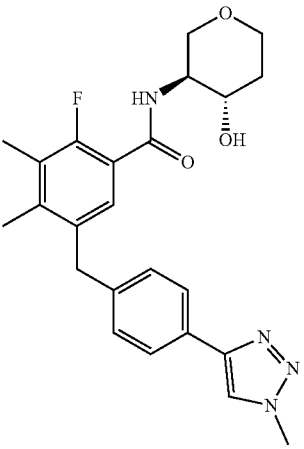 [SMILES: Cc1c(Cc2ccc(-c3cn(C)nn3)cc2)cc(C(=O)N[C@H]2COCC[C@@H]2O)c(F)c1C] | 439.2 |

TABLE 1-continued

| Ex. No. | IUPAC name | structural formula | MS |
|---|---|---|---|
| 43 | 1,5-anhydro-2,4-dideoxy-2-((5-(4-(1,3-dimethyl-1H-pyrazol-4-yl)benzyl)-2-fluoro-3,4-dimethylbenzoyl)amino)-L-threo-pentitol | | 452.3 |
| 44 | 4-cyano-N-((1S,2S)-2-hydroxycyclohexyl)-2-methoxy-3-methyl-5-(4-(1-methyl-1H-1,2,3-triazol-4-yl)benzyl)benzamide | | 460.3 |
| 45 | 3-chloro-N-((1S,2S)-2-hydroxycyclohexyl)-2-methoxy-4-methyl-5-((6-(1H-pyrazol-1-yl)pyridin-3-yl)methyl)benzamide | | 455.3 |

TABLE 1-continued

| Ex. No. | IUPAC name | structural formula | MS |
|---|---|---|---|
| 46 | 3-chloro-5-((6-(1,3-dimethyl-1H-pyrazol-4-yl)pyridin-3-yl)methyl)-N-((1S,2S)-2-hydroxycyclohexyl)-2-methoxy-4-methylbenzamide | | 483.3 |
| 47 | 3-chloro-N-((1S,2S)-2-hydroxycyclohexyl)-2-methoxy-4-methyl-5-((6-(1-methyl-1H-pyrazol-3-yl)pyridin-3-yl)methyl)benzamide | | 469.3 |

Experimental Example 1

Measurement of M1 Receptor Positive Allosteric Modulator (M1PAM) Activity

The activity of a test compound in the presence of acetylcholine at EC20 concentration (final concentration 0.8-1.0 nM), which affords an action corresponding to about 20% of the maximum activity, was measured as PAM activity. The method is as follows. CHO-K1 cells stably expressing a human M1 receptor (hCHRM1) were plated on a 384-well black clear bottom plate (BD Falcon) at 5,000 cells/well, and cultured in an incubator at 37° C., 5% $CO_2$ for 1 day. The medium in the cell plate was removed, and assay buffer A containing a calcium indicator (Recording medium (DOJINDO LABORATORIES), 0.1% BSA (Wako Pure Chemical Industries, Ltd.), 2.5 µg/mL Fluo-4 AM (DOJINDO LABORATORIES), 0.08% Pluronic F127 (DOJINDO LABORATORIES) and 1.25 mM probenecid (DOJINDO LABORATORIES) were added at 30 µL/well. The cells were left standing in the incubator at 37° C., 5% $CO_2$ for 30 min, and further left standing at room temperature for 30 min. A test compound prepared by diluting with assay buffer B (HBSS (Invitrogen), 20 mM HEPES (Invitrogen), 0.1% BSA) containing 3.2-4.0 nM acetylcholine was added at 10 µL/well, and the fluorescence was measured by FDSS/pcell (Hamamatsu Photonics K.K.) for 1 min every for 1 second. With the definition that the amount of change in the fluorescence on addition of acetylcholine (final concentration 1 µM) is 100% and that on addition of DMSO instead of a test compound is 0%, the activity (%) of the test compound was calculated, and the inflection point in the concentration-dependent curve of the test compound was calculated as IP values. The results are shown in Table 2.

TABLE 2

| Ex. No. | IP value (nM) | activity (%) at 10 µM |
|---|---|---|
| 2 | 95 | 96 |
| 4 | 23 | 108 |
| 5 | 12 | 105 |
| 6 | 23 | 107 |
| 10 | 4.8 | 106 |
| 11 | 37 | 97 |
| 12 | 19 | 103 |
| 13 | 9.4 | 102 |
| 14 | 8.6 | 98 |
| 15 | 14 | 100 |
| 16 | 30 | 99 |
| 17 | 40 | 99 |
| 18 | 27 | 97 |
| 19 | 84 | 93 |
| 20 | 31 | 97 |
| 21 | 10 | 96 |
| 22 | 55 | 95 |
| 24 | 2.6 | 95 |
| 25 | 33 | 97 |
| 26 | 31 | 99 |
| 27 | 39 | 100 |
| 28 | 20 | 100 |
| 29 | 48 | 97 |

TABLE 2-continued

| Ex. No. | IP value (nM) | activity (%) at 10 μM |
|---|---|---|
| 31 | 67 | 97 |
| 32 | 16 | 101 |

As shown in Table 2, the compound of the present invention has a superior cholinergic muscarine M1 receptor positive allosteric modulator activity.

Formulation Example 1

| | |
|---|---|
| (1) Compound obtained in Example 1 | 10.0 g |
| (2) Lactose | 60.0 g |
| (3) Cornstarch | 35.0 g |
| (4) Gelatin | 3.0 g |
| (5) Magnesium stearate | 2.0 g |

A mixture of the compound (10.0 g) obtained in Example 1, lactose (60.0 g) and cornstarch (35.0 g) is granulated by passing through a 1 mm mesh sieve while using 10 wt % aqueous gelatin solution (30 mL) (3.0 g as gelatin) and the granules are dried at 40° C. and sieved again. The obtained granules are mixed with magnesium stearate (2.0 g) and the mixture is compressed. The obtained core tablets are coated with a sugar coating of an aqueous suspension of saccharose, titanium dioxide, talc and gum arabic. The coated tablets are glazed with beeswax to give 1000 coated tablets.

Formulation Example 2

| | |
|---|---|
| (1) Compound obtained in Example 1 | 10.0 g |
| (2) Lactose | 70.0 g |
| (3) Cornstarch | 50.0 g |
| (4) Soluble starch | 7.0 g |
| (5) Magnesium stearate | 3.0 g |

The compound (10.0 g) obtained in Example 1 and magnesium stearate (3.0 g) are granulated using aqueous soluble starch solution (70 mL) (7.0 g as soluble starch), and the obtained granules are dried, and mixed with lactose (70.0 g) and cornstarch (50.0 g). The mixture is compressed to give 1000 tablets.

INDUSTRIAL APPLICABILITY

The compound of the present invention is useful as a cholinergic muscarinic M1 receptor positive allosteric modulator, or a medicament such as a prophylactic or therapeutic drug for Alzheimer's disease, schizophrenia, pain, sleep disorder, Parkinson's disease dementia, dementia with Lewy bodies and the like.

This application is based on a patent application Nos. 2016-048866 and 2016-134234 filed in Japan, the entire contents of which are incorporated by reference herein.

The invention claimed is:

1. A compound represented by the formula:

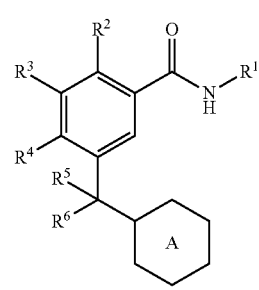

(I)

wherein
$R^1$ is (A) a $C_{1-6}$ alkyl group substituted by 1 to 3 substituents selected from (1) a halogen atom, (2) a hydroxy group, (3) an optionally substituted $C_{3-10}$ cycloalkyl group, and (4) an optionally substituted non-aromatic heterocyclic group, (B) an optionally substituted $C_{3-10}$ cycloalkyl group, or (C) an optionally substituted non-aromatic heterocyclic group;
$R^2$ is a fluorine atom or an optionally substituted $C_{1-6}$ alkoxy group;
$R^3$ is a hydrogen atom, a halogen atom, a cyano group, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted $C_{3-10}$ cycloalkyl group, or an optionally substituted $C_{3-10}$ cycloalkyloxy group;
$R^4$ is a hydrogen atom, a halogen atom, a cyano group, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted $C_{3-10}$ cycloalkyl group, or an optionally substituted $C_{3-10}$ cycloalkyloxy group;
$R^5$ and $R^6$ are each independently a hydrogen atom or a halogen atom; and
ring A is an optionally further substituted benzene ring or an optionally further substituted 6-membered aromatic heterocycle (excluding N-(2,3-dihydro-1,4-benzodioxin-6-yl)-5-(4-fluorobenzyl)-2-methoxybenzamide) or a salt thereof.

2. The compound according to claim 1, wherein $R^1$ is an optionally substituted 3- to 8-membered monocyclic non-aromatic heterocyclic group, or a salt thereof.

3. The compound according to claim 1, wherein $R^1$ is (A) a $C_{1-6}$ alkyl group substituted by 1 to 3 substituents selected from non-aromatic heterocyclic groups, (B) a non-cross-linked $C_{3-10}$ cycloalkyl group optionally substituted by a hydroxy group, or (C) a 3- to 8-membered monocyclic non-aromatic heterocyclic group optionally substituted by a hydroxy group;
$R^2$ is
a fluorine atom, or
a $C_{1-6}$ alkoxy group optionally substituted by 1 to 3 substituents selected from a halogen atom and a $C_{3-10}$ cycloalkyl group;
$R^3$ is a hydrogen atom, a halogen atom or a $C_{1-6}$ alkyl group;
$R^4$ is a cyano group or a $C_{1-6}$ alkyl group;
$R^5$ and $R^6$ are both hydrogen atoms; and ring A is
a benzene ring optionally further substituted by 1 to 3 substituents selected from 5- to 14-membered aromatic heterocyclic groups optionally substituted by 1 to 3 $C_{1-6}$ alkyl groups, or
a 6-membered aromatic heterocycle optionally further substituted by 1 to 3 substituents selected from a $C_{1-6}$ alkyl group and a 5- to 14-membered aromatic heterocyclic group optionally substituted by 1 to 3 $C_{1-6}$ alkyl groups, or a salt thereof.

4. The compound according to claim 1, wherein $R^1$ is a non-crosslinked $C_{3-10}$ cycloalkyl group optionally substituted by a hydroxy group or a 3- to 8-membered monocyclic non-aromatic heterocyclic group optionally substituted by a hydroxy group;
$R^2$ is a fluorine atom or a $C_{1-6}$ alkoxy group;
$R^3$ is a halogen atom or a $C_{1-6}$ alkyl group;
$R^4$ is a $C_{1-6}$ alkyl group;
$R^5$ and $R^6$ are both hydrogen atoms; and
ring A is a benzene ring optionally further substituted by 1 to 3 substituents selected from 5- to 14-membered aromatic heterocyclic groups optionally substituted by 1 to 3 $C_{1-6}$ alkyl groups, or a salt thereof.

5. The compound according to claim 4, wherein $R^1$ is

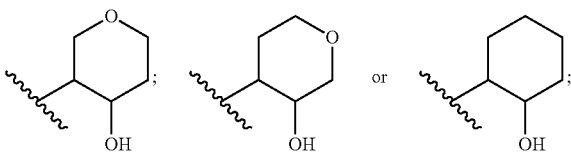 [SMILES: *C1COCCC1O ; *C1CCOCC1O ; *C1CCCCC1O]

and
ring A is a benzene ring optionally further substituted by 1 to 3 substituents selected from 5- or 6-membered monocyclic aromatic heterocyclic groups optionally substituted by 1 to 3 $C_{1-6}$ alkyl groups, or a salt thereof.

6. The compound according to claim 1, wherein $R^1$ is

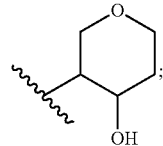 [SMILES: *C1COCCC1O]

$R^2$ is a fluorine atom or a $C_{1-6}$ alkoxy group;
$R^3$ is a $C_{1-6}$ alkyl group;
$R^4$ is a $C_{1-6}$ alkyl group;
$R^5$ and $R^6$ are both hydrogen atoms; and
ring A is a benzene ring further substituted by a 5- or 6-membered monocyclic aromatic heterocyclic group optionally substituted by one $C_{1-6}$ alkyl group, or a salt thereof.

7. 2-Fluoro-N-((3S,4S)-4-hydroxytetrahydro-2H-pyran-3-yl)-3,4-dimethyl-5-(4-(1H-pyrazol-1-yl)benzyl)benzamide, or a salt thereof.

8. N-((3S,4S)-4-hydroxytetrahydro-2H-pyran-3-yl)-2-methoxy-3,4-dimethyl-5-(4-(1-methyl-1H-1,2,3-triazol-4-yl)benzyl)benzamide, or a salt thereof.

9. A pharmaceutical composition comprising the compound according to claim 1 or a salt thereof and pharmaceutical acceptable carrier.

10. A method of cholinergic muscarinic M1 receptor positive allosteric modulation in a mammal, comprising administering an effective amount of the compound according to claim 1 or a salt thereof to the mammal.

11. A method for the treatment of Alzheimer's disease, schizophrenia, pain, sleep disorder, Parkinson's disease dementia, or dementia with Lewy bodies in a mammal, comprising administering an effective amount of the compound according to claim 1 or a salt thereof to the mammal.

* * * * *